(12) United States Patent
Mylari

(10) Patent No.: US 6,294,538 B1
(45) Date of Patent: Sep. 25, 2001

(54) COMPOUNDS FOR TREATING AND PREVENTING DIABETIC COMPLICATIONS

(75) Inventor: Banavara L. Mylari, Waterford, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 09/537,254

(22) Filed: Mar. 29, 2000

Related U.S. Application Data

(60) Provisional application No. 60/127,430, filed on Apr. 1, 1999.

(51) Int. Cl.$^7$ .................................................. A01N 43/58
(52) U.S. Cl. ...................................... 514/252.14; 540/295
(58) Field of Search ..................................... 574/255, 256, 574/252.14; 540/295

(56) References Cited

U.S. PATENT DOCUMENTS

| | | | |
|---|---|---|---|
| 5,138,058 | 8/1992 | Geisen et al. | 544/295 |
| 5,215,990 | 6/1993 | Geisen et al. | 514/255 |
| 5,728,704 | 3/1998 | Mylari et al. | 514/256 |
| 5,866,578 | 2/1999 | Mylari et al. | 514/256 |

FOREIGN PATENT DOCUMENTS

| | | | |
|---|---|---|---|
| 0384370 | 8/1990 | (EP) | C07D/239/42 |

OTHER PUBLICATIONS

S. Ao et al., Metabolism, 40, 77–87, 1991.
N. E. Cameron and M. A. Cotter, Diabetic Medicine, 8, Suppl. 1, 35A–36A, 1991.
D. J. Brown, The Pyrimidines, 1962.

*Primary Examiner*—James H. Reamer
(74) *Attorney, Agent, or Firm*—Peter C. Richardson; Gregg C. Benson; Martha G. Munchhof

(57) ABSTRACT

This invention is directed to sorbitol dehydrogenase inhibitory compounds of the formula I,

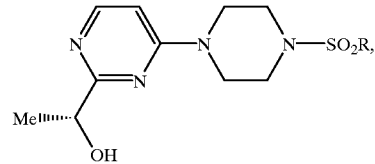

I wherein R is as defined in the specification. This invention is also directed to pharmaceutical compositions containing those compounds and methods of treating or preventing diabetic complications, particularly diabetic neuropathy, diabetic nephropathy and diabetic cardiomyopathy by administering such compounds to a mammal suffering from diabetes and therefore at risk for developing such complications. This invention is also directed to pharmaceutical compositions comprising a combination of a compound of formula I of this invention with an aldose reductase inhibitor and to methods of treating or preventing diabetic complications therewith. This invention is also directed to pharmaceutical compositions comprising a combination of a compound of formula I of this invention with an NHE-1 inhibitor and to methods of treating cardiomyopathy and other heart-related problems therewith. This invention is also directed to certain intermediates used in the synthesis of the compounds of formula I and to processes for preparing those intermediates.

46 Claims, No Drawings

COMPOUNDS FOR TREATING AND PREVENTING DIABETIC COMPLICATIONS

This application is filed claiming priority from co-pending Provisional Application No. 60/127,430 filed Apr. 1, 1999.

BACKGROUND OF THE INVENTION

The present invention relates to novel pyrimidine derivatives and to the use of such derivatives and related compounds to inhibit sorbitol dehydrogenase, lower fructose levels, or treat or prevent diabetic complications such as diabetic neuropathy, diabetic retinopathy, diabetic nephropathy, diabetic cardiomyopathy, diabetic microangiopathy and diabetic macroangiopathy in mammals. This invention also relates to pharmaceutical compositions and combinations comprising a sorbitol dehydrogenase inhibitor of formula I and an aldose reductase inhibitor and the use of such compositions or combinations to treat diabetic complications. This invention also relates to pharmaceutical compositions containing such pyrimidine derivatives and related compounds. This invention also relates to pharmaceutical compositions and combinations comprising a combination of a sorbitol dehydrogenase inhibitor of formula I and an NHE-1 inhibitor and to the use of such compositions or combinations to reduce tissue damage resulting from ischemia, and particularly to prevent perioperative myocardial ischemic injury.

S. Ao et al., *Metabolism*, 40, 77–87 (1991) have shown that significant functional improvement in the nerves of diabetic rats (based on nerve conduction velocity) occurs when nerve fructose levels are pharmacologically lowered, and that such improvement correlates more closely with the lowering of nerve fructose than the lowering of nerve sorbitol. Similar results were reported by N. E. Cameron and M. A. Cotter, *Diabetic Medicine*, 8, Suppl. 1, 35A–36A (1991). In both of these cases, lowering of nerve fructose was achieved using relatively high does of aldose reductase inhibitors, which inhibit the formation of sorbitol, a precursor of fructose, from glucose via the enzyme aldose reductase.

U.S. Pat. Nos. 5,138,058 and 5,215,990, which are hereby incorporated by reference, each disclose compounds of the formula

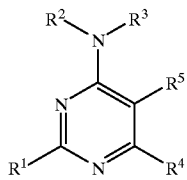

where $R^1$, $R^2$, $R^3_1$, $R^4$ and $R^5$ are as disclosed therein. Said compounds are disclosed as having utility as tools in screening for aldose reductase inhibitors due to the sorbitol accumulating activity of said compounds.

Commonly assigned U.S. Pat. Nos. 5,728,704 and 5,866,578 which are hereby incorporated by reference, discloses a method for treating or preventing diabetic complications that can be treated or prevented by inhibiting the enzyme sorbitol dehydrogenase. That patent also discloses compounds of the formula A,

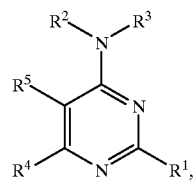

wherein $R^1$ through $R^5$ are defined as disclosed therein.

Further, U.S. Patent Nos., assigned to Hoechst, disclose as having utility in detecting levels of sorbitol dehydrogenase.

We have found that pyrimidine derivatives of the formulas I, II, III and IV, as defined below, and their pharmaceutically acceptable salts, lower fructose levels in the tissues of mammals affected by diabetes (e.g., nerve, kidney and retina tissue) and are useful in the treatment and prevention of the diabetic complications referred to above. These compounds, or their metabolites in vivo, are inhibitors of the enzyme sorbitol dehydrogenase, which catalyzes the oxidation of sorbitol to fructose.

SUMMARY OF THE INVENTION

This invention is directed to a compound of formula I,

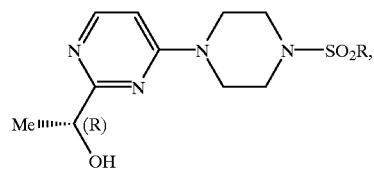

a prodrug thereof or a pharmaceutically acceptable salt of said compound or said prodrug, wherein:

R is N,N-dimethylamino or isopropyl.

A preferred compound of formula I is the compound of the formula

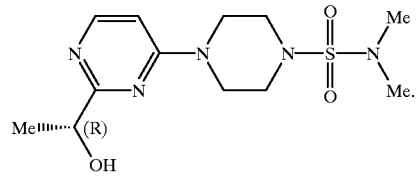

Another preferred compound of formula I is the compound of the formula

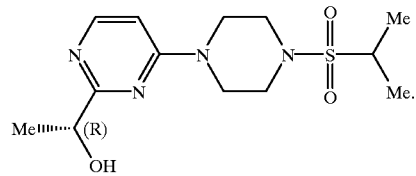

This invention is also directed to a pharmaceutical composition, designated Composition A, comprising a compound of formula I, a prodrug thereof or a pharmaceutically acceptable salt of said compound or said prodrug and a pharmaceutically acceptable carrier or diluent.

This invention is also directed to a method, designated Method A, of inhibiting sorbitol dehydrogenase in a mammal in need of such inhibition comprising administering to said mammal a sorbitol dehydrogenase inhibiting amount of a compound of formula I, a prodrug thereof or a pharmaceutically acceptable salt of said prodrug or said compound.

This invention is also directed to a method of treating diabetes in a mammal suffering from diabetes comprising administering to said mammal an effective amount of a compound of formula I, a prodrug thereof or a pharmaceutically acceptable salt of said prodrug or said compound.

This invention is also directed to a method, designated Method B, of treating or preventing diabetic complications in a mammal comprising administering to said mammal an effective amount of a compound of formula I, a prodrug thereof or a pharmaceutically acceptable salt of said prodrug or said compound.

A preferred method of Method B is wherein said mammal is suffering from diabetes.

Another preferred method of Method B is wherein said diabetic complication is diabetic neuropathy.

Another preferred method of Method B is wherein said diabetic complication is diabetic nephropathy.

Another preferred method of Method B is wherein said diabetic complication is diabetic retinopathy.

Another preferred method of Method B is wherein said diabetic complication is foot ulcers.

Another preferred method of Method B is wherein said diabetic complication is a cardiovascular condition.

This invention is also directed to a pharmaceutical composition, designated Composition B, comprising a compound of formula I, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

A preferred composition within Composition B additionally comprises a pharmaceutically acceptable carrier or diluent.

This invention is also directed to a method of treating diabetes in a mammal suffering from diabetes comprising administering to said mammal an effective amount of a compound of formula I, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

This invention is also directed to a method, designated Method C, of treating or preventing diabetic complications in a mammal comprising administering to said mammal an effective amount of a compound of formula I, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

A preferred method within Method C is wherein said mammal is suffering from diabetes.

Another preferred method within Method C is wherein said diabetic complication is diabetic neuropathy.

Another preferred method within Method C is wherein said diabetic complication is diabetic nephropathy.

Another preferred method within Method C is wherein said diabetic complication is diabetic retinopathy.

Another preferred method within Method C is wherein said diabetic complication is foot ulcers.

Another preferred method within Method C is wherein said diabetic complication is a cardiovascular condition.

This invention is also directed to a pharmaceutical composition, designated Composition C, comprising a compound of formula I, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

This invention is also directed to a method, designated Method D, of treating ischemia in a mammal suffering from ischemia comprising administering to said mammal an effective amount of a compound of formula I, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

A preferred method within Method D is wherein said ischemia is perioperative myocardial ischemia.

This invention is also directed to a method, designated Method E, of treating or preventing diabetic complications in a mammal comprising administering to said mammal an effective amount of a compound of formula I, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

A preferred method within Method E is wherein said mammal is suffering from diabetes.

Another preferred method within Method E is wherein said diabetic complication is diabetic neuropathy.

Another preferred method within Method E is wherein said diabetic complication is diabetic nephropathy.

Another preferred method within Method E is wherein said diabetic complication is diabetic retinopathy.

Another preferred method within Method E is wherein said diabetic complication is foot ulcers.

Another preferred method within Method E is wherein said diabetic complication is a cardiovascular condition.

This invention is also directed to a method of treating diabetes in a mammal suffering from diabetes comprising administering to said mammal an effective amount of a compound of formula I, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

This invention is also directed to a kit comprising:

a. a compound of formula I, a prodrug thereof or a pharmaceutically acceptable salt of said prodrug or said compound in a first unit dosage form;

b. an aldose reductase inhibitor, a prodrug thereof or a pharmaceutically acceptable salt of said prodrug or said aldose reductase inhibitor in a second unit dosage form; and c. a container.

This invention is also directed to a kit comprising:

a. a compound of formula I, a prodrug thereof or a pharmaceutically acceptable salt of said prodrug or said compound in a first unit dosage form;

b. a sodium hydrogen ion exchange (NHE-1) inhibitor, a prodrug thereof or a pharmaceutically acceptable salt of said prodrug or said NHE-1 inhibitor in a second unit dosage form; and a container.

A method of inhibiting sorbitol dehydrogenase in a mammal in need thereof comprising administering to said mammal Composition A.

A method of treating ischemia in a mammal suffering from ischemia comprising administering to said mammal Composition C.

A method of treating or preventing diabetic complications in a mammal comprising administering to said mammal Composition A.

A method of treating or preventing diabetic complications in a mammal comprising administering to said mammal Composition B.

A method of treating or preventing diabetic complications in a mammal comprising administering to said mammal Composition C.

A compound of the formula II,

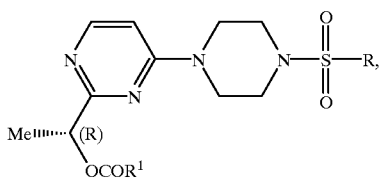

II wherein:

R is N,N-dimethylamino or isopropyl; and $R^1$ is $(C_1-C_4)$alkyl, benzyl or phenyl, said benzyl and phenyl being optionally substituted with up to three $(C_1-C_4)$alkyl, $(C_1-C_4)$alkoxy, halo or nitro.

This invention is also directed to a compound of the formula III,

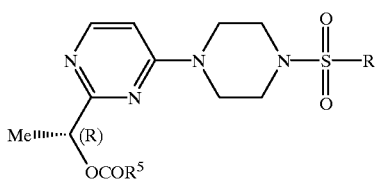

III wherein:

R is N,N-dimethylamino or isopropyl; and $R^5$ is

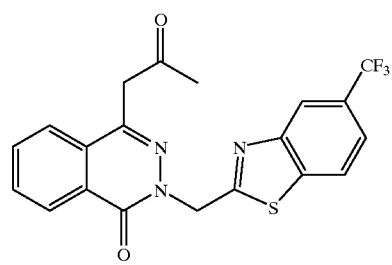

This invention is also directed to a compound of the formula IV:

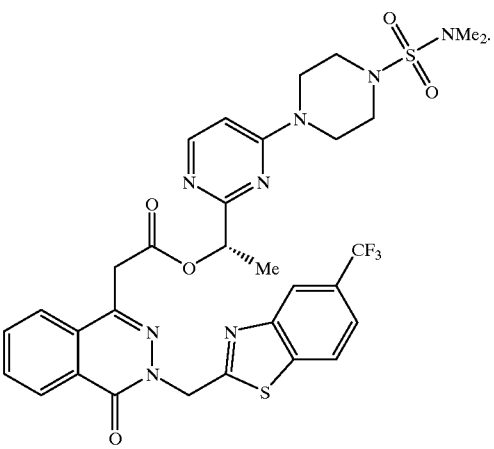

This invention is also directed to a pharmaceutical composition comprising a compound of formula I, a prodrug thereof or a pharmaceutically acceptable salt of said prodrug or said compound, and a glycogen phosphorylase inhibitor (GPI), a prodrug of said GPI or a pharmaceutically acceptable salt of said GPI or said prodrug.

This invention is also directed to a kit comprising:
a. a compound of formula I, a prodrug thereof or a pharmaceutically acceptable salt of said prodrug or said compound in a first unit dosage form;
b. a glycogen phosphorylase inhibitor (GPI), a prodrug thereof or a pharmaceutically acceptable salt of said prodrug or said GPI in a second unit dosage form; and
c. a container.

This invention is also directed to a pharmaceutical composition comprising a compound of Formula I, a prodrug thereof or a pharmaceutically acceptable salt of said compound or said prodrug, and a pharmaceutically acceptable carrier or diluent.

Diabetic complications which are preferably treated by the method of this invention include diabetic cardiomyopathy, diabetic neuropathy, diabetic nephropathy, diabetic retinopathy and foot ulcers.

The term "reduction" is intended to include partial prevention or prevention which, although greater than that which would result from taking no compound or from taking a placebo, is less than 100% in addition to substantially total prevention.

The term "damage resulting from ischemia" as employed herein refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and/ or necrosis. Alternatively, where blood flow or organ perfusion may be quantitatively adequate, the oxygen carrying capacity of the blood or organ perfusion medium may be reduced, e.g., in hypoxic environment, such that oxygen supply to the tissue is lowered, and impaired tissue performance, tissue dysfunction, and/or tissue necrosis ensues.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which following administration, release the drug in vivo via some chemical or physiological process (e.g., a prodrug on being brought to the physiological pH or through enzyme action is converted to the desired drug form).

By halo is meant chloro, bromo, iodo, or fluoro.

By alkyl is meant straight chain saturated hydrocarbon or branched saturated hydrocarbon. Exemplary of such alkyl groups (assuming the designated length encompasses the particular example) are methyl, ethyl, propyl, isopropyl, butyl, sec-butyl and tertiary butyl.

By alkoxy is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy and tertiary butoxy.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. Where more than one basic moiety exists the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

As used herein, the expressions "reaction inert solvent" and "inert solvent" refers to a solvent or mixture of solvents which does not interact with starting materials, reagents, intermediates or products in a manner which adversely affects the yield of the desired product.

DMF means N,N-dimethylformamide. DMSO means dimethyl sulfoxide. THF means tetrahydrofuran.

The subject invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

Other features and advantages will be apparent from the specification and claims which describe the invention.

DETAILED DESCRIPTION OF THE INVENTION

In general the compounds of this invention can be made by processes which include processes known in the chemical arts, particularly in light of the description contained herein. Certain processes for the manufacture of the compounds of this invention are provided as further features of the invention and are illustrated by the following reaction schemes. Other processes are described in the experimental section.

The compounds of this invention may be prepared as illustrated in Scheme 1 below. Compounds of formula 1-10, Scheme I, in which $R^1$ is hydrogen, $(C_1-C_6)$alkyl, $CO(C_1-C_6)$alkyl, CO-phenyl or benzyl; said benzyl and phenyl are optionally substituted on the phenyl ring with up two substituents selected from $(C_1-C_4)$alkyl, fluoro, chloro, bromo, iodo, trifluoromethyl or $(C_1-C_4)$alkoxy; and $R^4$ is N,N-dimethylamino or isopropyl can be prepared according to Scheme I.

Scheme 1

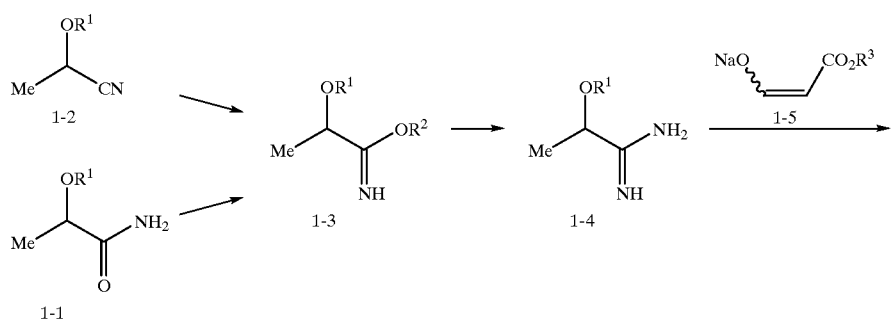

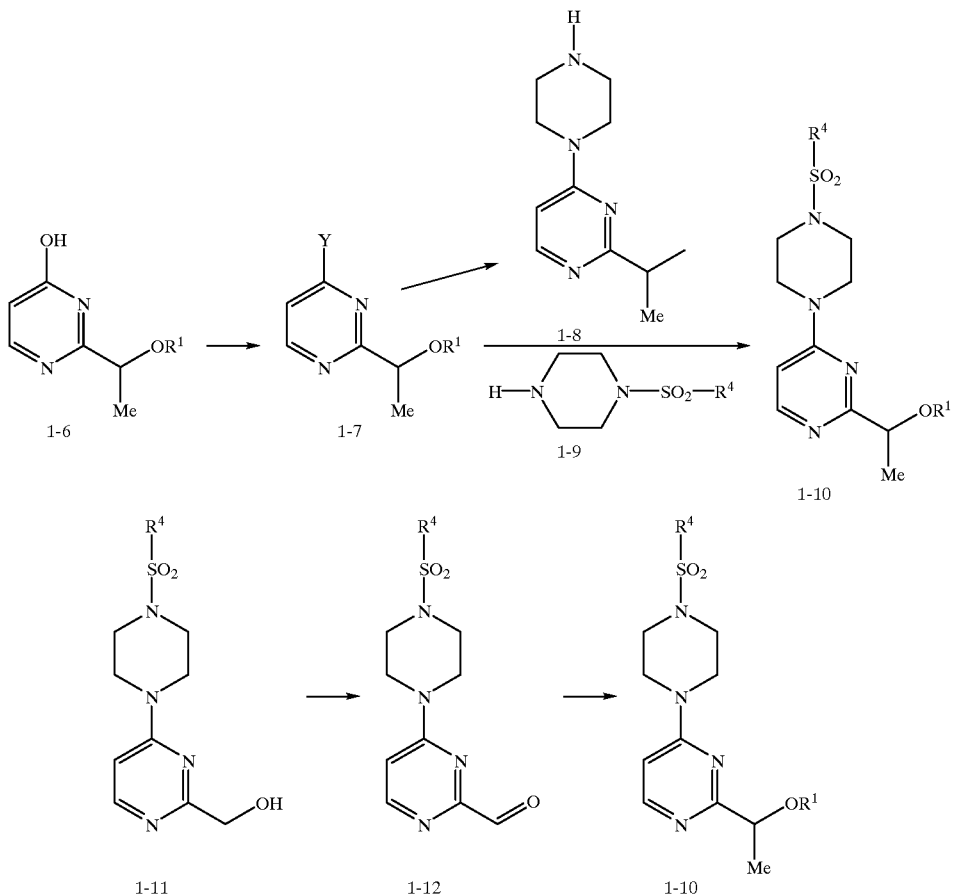

Compounds of formula 1-3 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy and $R^2$ is ethyl or methyl can be prepared by reacting compounds of formula 1-1 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy with Meerwein's reagent under standard conditions and are usually isolated in the form of their acid addition salts, for example, a hydrochloride or a tetrafluoroborate salt.

Compounds of formula 1-3 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy and $R^2$ is ethyl or methyl can also be prepared by reacting compounds of formula 1-2 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy with gaseous hydrogen chloride in the presence of alcoholic solvents such as ethanol or methanol. The quantity of gaseous hydrogen chloride could range from one equivalent up to that required to saturate the solvent employed. The reaction is conducted at ambient pressure and at temperatures from between −20° C. to 0° C. The term ambient pressure means the pressure of the room in which the reaction is being conducted.

Compounds of formula 1-4 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy can be prepared by reacting compounds of formula 1-3 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy with ammonia in alcoholic solvents. Typical alcoholic solvents include methanol, ethanol, propanols, and butanols. The reaction is conducted at temperatures between −20° to 0° C.

Compounds of formula 1-6 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy are prepared by reacting compounds of formula 1-4 wherein $R^1$ is H, $(C_1–C_4)$alkyl or benzyl optionally substituted on the phenyl ring with up two substituents selected from $(C_1–C_4)$alkyl, fluoro, chloro, bromo, iodo, trifluoromethyl or $(C_1–C_4)$alkoxy with compounds of formula 1-5 (which are prepared according to the method disclosed in U.S. Pat. No. 5,138,058) wherein $R^3$ is $(C_1–C_4)$alkyl. The reaction can be conducted in aqueous or alcoholic solvents, at temperatures from between 25 and 100° C. Typical alcoholic solvents include methanol, ethanol, propanols, and butanols.

Compounds of formula 1-6 of R enantiomeric configuration in which $R^1$ is CO—$(C_1–C_6)$alkyl, CO-phenyl wherein phenyl is optionally substituted with up to two substituents selected from $(C_1–C_4)$alkyl, fluoro, chloro, bromo, iodo, trifluoromethyl or $COCH_2$-phenyl wherein said phenyl is optionally substituted with $(C_1–C_4)$alkyl, fluoro, chloro, bromo, iodo, trifluoromethyl or $(C_1-C_4)$ alkoxy are prepared by reacting compounds of formula 1-6 which are racemic, i.e., a mixture of R and S enantiomers, wherein $R^1$ is H with compounds of formula $CH_2=CH—OR^1$ wherein $R^1$ is $CO(C_1-C_6)$alkyl, CO-phenyl wherein phenyl is optionally substituted with $(C_1-C_4)$alkyl, fluoro, chloro, bromo, iodo, trifluoromethyl or $(C_1-C_4)$alkoxy, $COCH_2$-phenyl wherein phenyl is optionally substituted with $(C_1-C_4)$alkyl, fluoro, chloro, bromo, iodo, trifluoromethyl or $(C_1-C_4)$alkoxy, and a lipase enzyme, optionally in the presence of a solvent. Generally, the reaction is conducted in the presence of from between one to 100 equivalents of $CH_2=CH—OR^1$ with or without a solvent. When a solvent is used it consists of organic solvents which include non-polar solvents such as $C_1-C_7$alkyl hydrocarbons or aromatic hydrocarbon solvents such as benzene, toluene and xylenes, polar solvents such as acetonitrile or dimethyl sulfoxide or ether solvents such as $(C_1-C_6)$alkyl ethers, tetrahydrofuran or dioxane. The preferred solvents are ether solvents. A variety of commercially available lipases, including Lipase P30, can be employed in the reaction and the proportion of lipase could range from between catalytic amounts up to 10 equivalents, The reaction is conducted at ambient pressure and at temperatures from 25° C. up to the refluxing temperature of either $CH_2=CH—OR^1$ or the solvent employed.

Compounds of formula 1-6 with R enantiomeric configuration in which $R^1$ is $CO(C_1-C_6)$alkyl, CO-phenyl wherein phenyl is optionally substituted with $(C_1-C_4)$alkyl, fluoro, chloro, bromo, iodo, or trifluoromethyl, $COCH_2$-phenyl wherein phenyl is optionally substituted with $(C_1-C_4)$alkyl, fluoro, chloro, bromo, iodo, trifluoromethyl $(C_1-C_4)$alkoxy can also be prepared by reacting compounds of formula 1-6 wherein $R^1$ is H with $(C_1-C_6)$alkyl-CO—O—CO—$(C_1-C_6)$ alkyl or $(C_1-C_6)$alkyl-COCl in the presence of a suitable base and reaction compatible solvents. Suitable bases include tertiary organic bases such as triethylamine, pyridine, and dimethylamino pyridine. Reaction compatible solvents include ether, tetrahydrofuran, and halocarbon solvents such as methylene chloride and chloroform.

Compounds of formula 1-7 wherein Y is Cl, $OSO_2Me$ and $OSO_2CF_3$, respectively, and $R^1$ is as defined above can be prepared by reacting compounds of formula 1-6 respectively, with phosphorus oxychloride, methanesulfonyl chloride, and trifluoromethanesulfonyl chloride. The reaction is conducted in reaction inert solvents such as methylene chloride, ether, or tetrahydrofuran and in the presence of a tertiary amine base such as triethylamine and pyridine. The reaction temperature is at between 0 to 30° C.

Compounds of formula 1-8 can be prepared by reacting compounds of formula 1-7 wherein Y is Cl, $SOO_2Me$ or $OSO_2CF_3$ with piperazine. The reaction is conducted in reaction inert solvents such as methylene chloride, ether, or tetrahydrofuran and in the presence of a tertiary amine base such as triethylamine, pyridine or an excess quantity of piperazine. The reaction temperature is from between 0 to 30° C.

Compounds of formula 1-10 wherein $R^1$ is $(C_1-C_6)$alkyl, benzyl optionally substituted on the phenyl ring with up two substituents selected from $(C_1-C_4)$alkyl, fluoro, chloro, bromo, iodo, trifluoromethyl or $(C_1-C_4)$alkoxy, $CO(C_1-C_6)$ alkyl, $(C_1-C_6)$aryl wherein aryl is optionally substituted phenyl with up two substituents selected from $(C_1-C_4)$alkyl, chloro, bromo, iodo, or trifluoromethyl can be prepared by reacting compounds of formula 1-8 with $R^4SO_2Cl$ wherein $R^4$ is N,N-dimethyl or isopropyl. The reaction is conducted in reaction inert solvents such as methylene chloride, ether, or tetrahydrofuran and in the presence of a tertiary amine base such as triethylamine, dimethylamino pyridine, pyridine or an excess quantity of 1-8. The reaction temperature is from between room temperature and the refluxing temperature of the solvent employed.

Compounds of formula 1-10 wherein $R^1$ is hydrogen and $R^4$ is N,N-dimethyl or isopropyl can be prepared by reacting compounds of formula 1-10 wherein $R^1$ is $CO(C_1-C_6)$alkyl, or $CO(C_1-C_6)$aryl wherein aryl is optionally substituted phenyl with up two substituents selected from $(C_1-C_4)$alkyl, chloro, bromo, iodo, trifluoromethyl or $(C_1-C_4)$alkoxy with a base or an acid in water or a mixture of water and water-miscible solvents. Water-miscible solvents include methanol, ethanol, propanol, DMSO, dioxane and tetrahydrofuran. Bases include alkali metal and alkaline earth metal hydroxides such as lithium, sodium, potassium, and calcium hydroxides. Acids include mineral acids such as hydrochloric and sulfuric acids. The reaction is carried out at temperatures from between room temperature and 50° C.

Compounds of formula 1-10 wherein $R^1$ is hydrogen and $R^4$ is N,N-dimethyl or isopropyl can be prepared by reacting compounds of formula 1-12 wherein $R^4$ is N,N-dimethyl or isopropyl with methyl magnesium bromide in standard reaction-inert solvents used in carrying out Grignard reactions, for example, ether or tetrahydrofuran. The reaction is carried out at temperatures from between 0° C. and the refluxing temperature of the solvent employed.

Compounds of formula 1-12 wherein $R^4$ is N,N-dimethyl or isopropyl can be prepared by oxidizing compounds of formula 1-11 (prepared according to U.S. Pat. No. 5,138, 058) wherein $R^4$ is N,N-dimethyl or isopropyl. Oxidation can be carried out with activated manganese-di-oxide in chlorinated solvents such as methylene chloride or using the well known Swern oxidation conditions.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature.

The compounds of the instant invention inhibit the formation of sorbitol dehydrogenase and as such have utility in the treatment of diabetic complications including but not limited to such complications as diabetic nephropathy, diabetic neuropathy and diabetic cardiomyopathy. The utility of the compounds of the present invention as medical agents in the treatment of diseases, such as are detailed herein in mammals (e.g., humans) for example, diabetic complications such as diabetic cardiomyopathy, diabetic neuropathy, diabetic nephropathy, diabetic microangiopathy and diabetic macroangiopathy is demonstrated by the activity of the compounds of formula I of this invention in conventional assays. Such assays also provide a means whereby the activities of the compounds of formula I of this invention can be compared with the activities of other known compounds. The results of these comparisons are useful for determining dosage levels in mammals, including humans, for the treatment of such diseases.

Measurement of SDH Activity

Male Sprague-Dawley rats (350–400 g) are used for these experiments. Diabetes is induced in some of the rats by a tail vein injection of streptozocin, 85 mg/kg. Twenty-four hours later, 4 groups of diabetic rats are given a single dose of 4-[4-(N,N-dimethylsulfamoyl)-piperazino]-2-methylpyrimidine (10, 50, 100, or 300 mg/kg) by oral gavage. Animals are sacrificed 4–6 hours after dosing and blood and sciatic nerves are harvested. Tissues and cells are extracted with 6% perchloric acid.

Sorbitol in erythrocytes and nerves is measured by a modification of the method of R. S. Clements et al. (Science, 166: 1007–8, 1969). Aliquots of tissue extracts are added to an assay system which has final concentrations of reagents of 0.033 M glycine, pH 9.4, 800 mM β-nicotine adenine dinucleotide, and 4 units/ml of sorbitol dehydrogenase. After incubation for 30 minutes at room temperature, sample fluorescence is determined on a fluorescence spectrophotometer with excitation at 366 nm and emission at 452 nm. After subtracting appropriate blanks, the amount of sorbitol in each sample is determined from a linear regression of sorbitol standards processed in the same manner as the tissue extracts.

Fructose is determined by a modification of the method described by M. Ameyama, *Methods in Enzymology*, 89: 20–25 (1982). Resazurin is substituted for ferricyanide. Aliquots of tissue extracts are added to the assay system, which has final concentrations of reagents of 1.2 M citric acid, pH 4.5, 13 mM resazurin, 3.3 units/ml of fructose dehydrogenase and 0.068% Triton X-100. After incubation for 60 minutes at room temperature, sample fluorescence is determined on a fluorescence spectrophotometer with excitation at 560 nm and emission at 580 nm. After subtracting appropriate blanks, the amount of fructose in each sample is determined from a linear regression of fructose standards processed in the same manner as the tissue extracts.

SDH activity is measured by a modification of the method described by U. Gerlach, *Methodology of Enzymatic Analyses*, edited by H. U. Bergmeyer, 3, 112–117 (1983). Aliquots of sera or urine are added to the assay system, which has final concentrations of reagents of 0.1 M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance is determined at 340 nm. SDH activity was presented as milliOD$_{340}$ units/minute (OD$_{340}$=optical density at 340 nm).

Any aldose reductase inhibitor may be used as the second compound (active agent) of this invention for combination therapies. The term aldose reductase inhibitor refers to compounds which inhibit the bioconversion of glucose to sorbitol catalyzed by the enzyme aldose reductase. Such inhibition is readily determined by those skilled in the art according to standard assays (J. Malone, *Diabetes*, 29:861–864, 1980. "Red Cell Sorbitol, an Indicator of Diabetic Control"). A variety of aldose reductase inhibitors are described and referenced below, however, other aldose reductase inhibitors will be known to those skilled in the art. The disclosures of U.S. patents listed below are hereby incorporated by reference. Also, common chemical USAN names or other designation are in parentheses where applicable, together with reference to appropriate patent literature disclosing the compound.

The activity of an aldose reductase inhibitor in a tissue can be determined by testing the amount of aldose reductase inhibitor that is required to lower tissue sorbitol (i.e., by inhibiting the further production of sorbitol consequent to blocking aldose reductase) or lower tissue fructose (by inhibiting the production of sorbitol consequent to blocking aldose reductase and consequently the production of fructose). While not wishing to be bound by any particular theory or mechanism, it is believed that an aldose reductase inhibitor, by inhibiting aldose reductase, prevents or reduces ischemic damage as described hereinafter.

Accordingly, examples of aldose reductase inhibitors useful in the compositions and methods of this invention include:

1. 3-(4-bromo-2-fluorobenzyl)-3,4-dihydro-4-oxo-1-phthalazineacetic acid (ponalrestat, U.S. Pat. No. 4,251,528);

2. N[[(5-trifluoromethyl)-6-methoxy-1-naphthalenyl] thioxomethyl}-N-methylglycine (tolrestat, U.S. Pat. No. 4,600,724);

3. 5-[(Z,E)-β-methylcinnamylidene]-4-oxo-2-thioxo-3-thiazolideneacetic acid (epalrestat, U.S. Pat. Nos. 4,464,382, 4,791,126, 4,831,045);

4. 3-(4-bromo-2-fluorobenzyl)-7-chloro-3,4-dihydro-2,4-dioxo-1(2H)-quinazolineacetic acid (zenarestat, U.S. Pat. Nos. 4,734,419, and 4,883,800);

5. 2R,4R-6,7-dichloro-4-hydroxy-2-methylchroman-4-acetic acid (U.S. Pat. No. 4,883,410);

6. 2R,4R-6,7-dichloro-6-fluoro-4-hydroxy-2-methylchroman-4-acetic acid (U.S. Pat. No. 4,883,410);

7. 3,4-dihydro-2,8-diisopropyl-3-oxo-2H-1,4-benzoxazine-4-acetic acid (U.S. Pat. No. 4,771,050);

8. 3,4dihydro-3-oxo-4-[(4,5,7-trifluoro-2-benzothiazolyl) methyl]-2H-1,4-benzothiazine-2-acetic acid (SPR-210, U.S. Pat. No. 5,252,572);

9. N-[3,5-dimethyl-4-[(nitromethyl)sulfonyl]phenyl]-2-methyl-benzeneacetamide (ZD5522, U.S. Pat. Nos. 5,270,342 and 5,430,060);

10. (S)-6-fluorospiro[chroman-4,4'-imidazolidine]-2,5'-dione (sorbinil, U.S. Pat. No. 4,130,714);

11. d-2-methyl-6-fluoro-spiro(chroman-4',4'-imidazolidine)-2',5'-dione (U.S. Pat. No. 4,540,704);

12. 2-fluoro-spiro(9H-fluorene-9,4'imidazolidine)2',5'-dione (U.S. Pat. No. 4,438,272);

13. 2,7-di-fluoro-spiro(9H-fluorene-9,4'imidazolidine)2',5'-dione (U.S. Pat. Nos. 4,436,745, 4,438,272);

14. 2,7-di-fluoro-5-methoxy-spiro(9H-fluorene-9,4'imidazolidine)2',5'-dione (U.S. Pat. Nos. 4,436,745, 4,438,272);

15. 7-fluoro-spiro(5H-indenol[1,2-b]pyridine-5,3'-pyrrolidine)2,5'-dione (U.S. Pat. Nos. 4,436,745, 4,438,272);

16. d-cis-6'-chloro-2',3'-dihydro-2'-methyl-spiro-(imidazolidine-4,4'-4'-H-pyrano(2,3-b)pyridine)-2,5-dione (U.S. Pat. No. 4,980,357);

17. spiro[imidazolidine-4,5'(6H)quinoline]2,5-dione-3'-chloro-7,'8'-dihydro-7'-methyl-(5'-cis) (U.S. Pat. No. 5,066,659);

18. (2S,4S)-6-fluoro-2',5'-dioxospiro(chroman-4,4'-imidazolidine)-2-carboxamide (U.S. Pat. No. 5,447,946); and 19. 2-[(4-bromo-2-fluorophenyl)methyl]-6-fluorospiro [isoquinoline-4(1H),3'-pyrrolidine]-1,2',3,5'(2H)-tetrone (ARI-509, U.S. Pat. No. 5,037,831).

Other aldose reductase inhibitors include compounds having formula ARI,

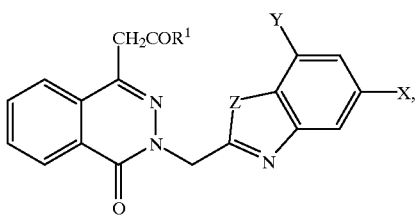

ARI or a pharmaceutically acceptable salt thereof, wherein

Z in the compound of formula ARI is O or S;

$R^1$ in the compound of formula ARI is hydroxy or a group capable of being removed in vivo to produce a compound of formula ARI wherein $R^1$ is OH; and X and Y in the compound of formula ARI are the same or different and are selected from hydrogen, trifluoromethyl, fluoro, and chloro.

A preferred subgroup within the above group of aldose reductase inhibitors includes numbered compounds 1, 2, 3, 4, 5, 6, 9, 10, and 17, and the following compounds of Formula ARI:

20. 3,4-dihydro-3-(5-fluorobenzothiazol-2-ylmethyl)-4-oxophthalazin-1-yl-acetic acid [$R^1$=hydroxy; X=F; Y=H];

21. 3-(5,7-difluorobenzothiazol-2-ylmethyl)-3,4-dihydro-4-oxophthalazin-1-ylacetic acid [$R^1$=hydroxy; X=Y=F];

22. 3-(5-chlorobenzothiazol-2-ylmethyl)-3,4-dihydro-4-oxophthalazin-1-ylacetic acid [$R^1$=hydroxy; X=Cl; Y=H];

23. 3-(5,7dichlorobenzothiazol-2-ylmethyl)-3,4-dihydro-4-oxophthalazin-1-ylacetic acid [$R^1$=hydroxy; X=Y=Cl];

24. 3,4-dihydro-4-oxo-3-(5-trifluoromethylbenzoxazol-2-ylmethyl)phthalazin-1-ylacetic acid [$R^1$=hydroxy; X=$CF_3$; Y=H];

25. 3,4dihydro-3-(5-fluorobenzoxazol-2-ylmethyl)-4-oxophthalazin-1-yl-acetic acid [$R^1$=hydroxy; X=F; Y=H];

26. 3-(5,7-difluorobenzoxazol-2-ylmethyl)-3,4-dihydro-4-oxophthalazin-1-ylacetic acid [$R^1$=hydroxy; X=Y=F];

27. 3-(5-chlorobenzoxazol-2-ylmethyl)-3,4-dihydro-4-oxophthalazin-1-ylacetic acid [$R^1$=hydroxy; X=Cl; Y=H];

28. 3-(5,7-dichlorobenzoxazol-2-ylmethyl)-3,4-dihydro-4-oxophthalazin-1-ylacetic acid [$R^1$=hydroxy; X=Y=Cl]; and 29. zopolrestat; 1-phthalazineacetic acid, 3,4-dihydro-4-oxo-3-[[5-trifluoromethyl)-2-benzothiazolyl]methyl]-[$R^1$=hydroxy; X=trifluoromethyl; Y=H].

In compounds 20–23, and 29 Z is S. In compounds 24–28, Z is O.

Of the above subgroup, compounds 20–29 are more preferred with 29 especially preferred.

An especially preferred aldose reductase inhibitor is 1-phthalazineacetic acid, 3,4-dihydro-4-oxo-3-[[5-trifluoromethyl)-2-benzothiazolyl]methyl]-.

The aldose reductase inhibitor compounds of this invention are readily available or can be easily synthesized by those skilled in the art using conventional methods of organic synthesis, particularly in view of the pertinent patent specification descriptions.

An amount of the aldose reductase inhibitor of this invention that is effective for the activities of this invention may be used. Typically, an effective dosage for the aldose reductase inhibitors of this invention is in the range of about 0.1 mg/kg/day to 100 mg/kg/day in single or divided doses, preferably 0.1 mg/kg/day to 20 mg/kg/day in single or divided doses.

Any sodium hydrogen ion exchange (NHE-1) inhibitor may be used as the second compound (active agent) of this invention for combination therapies. The term NHE-1 inhibitor refers to compounds which inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases (e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [(e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema. NHE-1 inhibitors can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries. The utility of NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of the compounds of formula I of this invention in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

NHE-1 inhibitors are disclosed in U.S. Pat. No. 5,698,581, European Patent Application Publication No. EP 803 501 A1, International Patent Application Publication Nos. WO 94/26709 and PCT/JP97/04650, each of which is incorporated herein by reference. The NHE-1 inhibitors disclosed therein have utility in the combination of this invention. Said NHE-1 inhibitors can be prepared as disclosed therein.

Preferred NHE-1 inhibitors include compounds of the formula NHE,

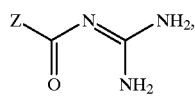

NHE a prodrug thereof or a pharmaceutically acceptable salt of said compound or of said prodrug, wherein Z in the compound of formula NHE is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z in the compound of formula NHE carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ in the compound of formula NHE are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$) alkyl, any of said previous ($C_1$–$C_4$)alkyl moieties optionally having from one to nine fluorines; said ($C_1$–$C_4$)alkyl or ($C_3$–$C_4$)cycloalkyl optionally mono-or di-substituted independently with hydroxy, ($C_1$–$C_4$) alkoxy, ($C_1$–$C_4$)alkylthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$) cycloalkyl optionally having from one to seven fluorines;

wherein M in the compound of formula NHE is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M in the compound of formula NHE is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$) alkoxy, ($C_1$–$C_4$)alkoxycarbonyl, ($C_1$–$C_4$)alkyl, formyl, ($C_1$–$C_4$)alkanoyl, ($C_1$–$C_4$)alkanoyloxy, ($C_1$–$C_4$) alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$)alkylthio, ($C_1$–$C_4$)alkylsulfinyl, ($C_1$–$C_4$) alkylsulfonyl, mono-N- or di-N,N-($C_1$–$C_4$) alkylaminosulfonyl, ($C_2$–$C_4$)alkenyl, ($C_2$–$C_4$)alkynyl or ($C_5$–$C_7$)cycloalkenyl, wherein said ($C_1$–$C_4$)alkoxy, ($C_1$–$C_4$)alkyl, ($C_1$–$C_7$) alkanoyl, ($C_1$–$C_4$)alkylthio, mono-N- or di-N,N-($C_1$–$C_4$)alkylamino or ($C_3$–$C_7$)cycloalkyl $R^6$, $R^7$ and $R^8$ substituents are optionally mono- substituted independently with hydroxy, ($C_1$–$C_4$)alkoxycarbonyl, ($C_3$–$C_7$)cycloalkyl, ($C_1$–$C_4$)alkanoyl, ($C_1$–$C_4$) alkanoylamino, ($C_1$–$C_4$)alkanoyloxy, ($C_1$–$C_4$) alkoxycarbonylamino, sulfonamido, ($C_1$–$C_4$) alkylsulfonamido, amino, mono-N- or di-N,N-($C_1$–$C_4$) alkylamino, carbamoyl, mono-N- or di-N,N-($C_1$–$C_4$) alkylcarbamoyl, cyano, thiol, nitro, ($C_1$–$C_4$)alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines.

Especially preferred NHE-1 inhibitors include [1-(8-bromoquinolin-5-yl)-5-cyclopropyl-1H-pyrazole-4-carbonyl]guanidine; [1-(6-chloroquinolin-5-yl)-5-cyclopropyl-1H-pyrazole-4-carbonyl]guanidine; [1-(indazol-7-yl)-5-cyclopropyl-1H-pyrazole-4carbonyl] guanidine; [1-(benzimidazol-5-yl)-5-cyclopropyl-1H-pyrazole-4-carbonyl]guanidine; [1-(1-isoquinolyl)-5-cyclopropyl-1H-pyrazole-4-carbonyl]guanidine; [5-cyclopropyl-1-(4-quinolinyl)-1H-pyrazole-4-carbonyl] guanidine; [5-cyclopropyl-1-(quinolin-5-yl)-1H-pyrazole-4-carbonyl]guanidine; [5-cyclopropyl-1-(quinolin-8-yl)-1H-pyrazole-4-carbonyl]guanidine; [1-(indazol-6-yl)-5-ethyl-1H-pyrazole-4-carbonyl]guanidine; [1-(indazol-5-yl)-5-ethyl-1H-pyrazole-4-carbonyl]guanidine; [1-(benzimidazol-5-yl)-5-ethyl-1H-pyrazole-4-carbonyl]guanidine; [1-(1-methylbenzimidazol-6-yl)-5ethyl-1H-pyrazole-4-carbonyl] guanidine; 1-(5-quinolinyl)-5-n-propyl-1H-pyrazole-4-carbonyl)guanidine; [1-(5-quinolinyl)-5-isopropyl-1H-pyrazole-4-carbonyl]guanidine; [5-ethyl-1-(6-quinolinyl)-1H-pyrazole-4-carbonyl]guanidine; [1-(2-methylbenzimidazol-5-yl)-5-ethyl-1H-pyrazole-4-carbonyl] guanidine; [1-(1,4-benzodioxan-6-yl)-5-ethyl-1H-pyrazole-4-carbonyl]guanidine; [1-(benzotriazol-5-yl)-5-ethyl-1H-pyrazole-4-carbonyl]guanidine; [1-(3-chloroindazol-5-yl)-5-ethyl-1H-pyrazole-4-carbonyl]guanidine; [1-(5-quinolinyl-5-butyl-1H-pyrazole-4-carbonyl]guanidine; [5-propyl-1-(6-quinolinyl)-1H-pyrazole-4-carbonyl] guanidine; [5-isopropyl-1-(6-quinolinyl)-1H-pyrazole-4-carbonyl]guanidine; or a pharmaceutically acceptable salt thereof.

The preferred and especially preferred NHE-1 inhibitors disclosed in the above two paragraphs can be prepared according to methods set forth in International Patent Application No. PCT/IB99/00206 or as set forth below, where the variables in the following schemes and description refer only to the NHE-1 compounds.

SCHEME I
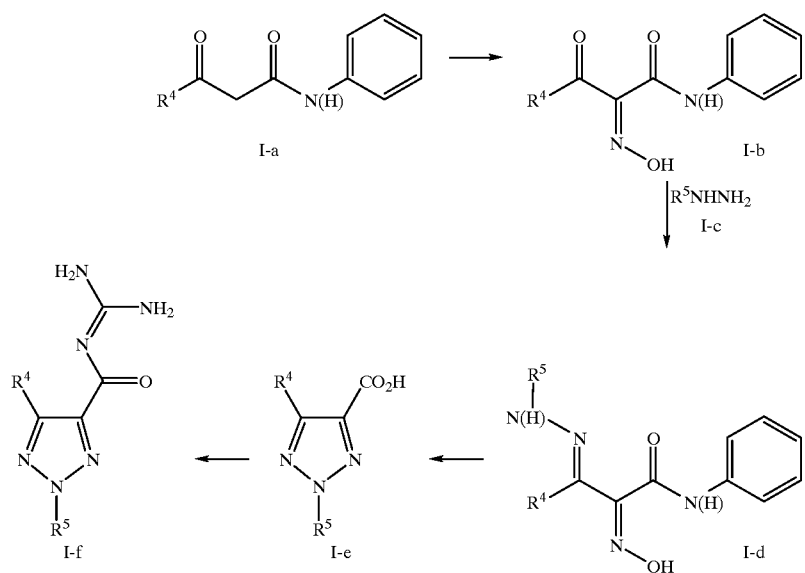
SCHEME II
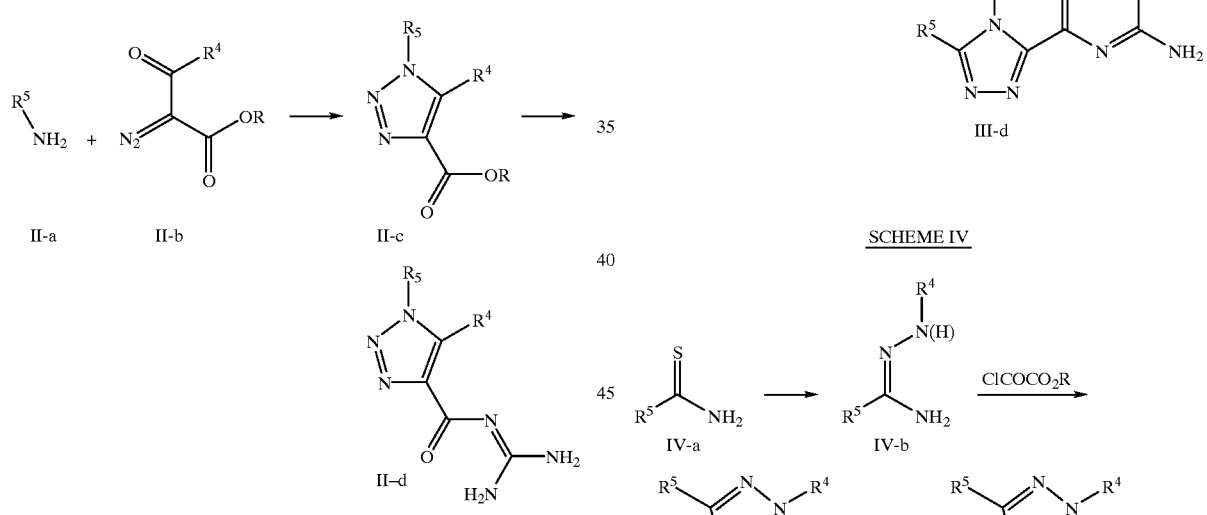
SCHEME III
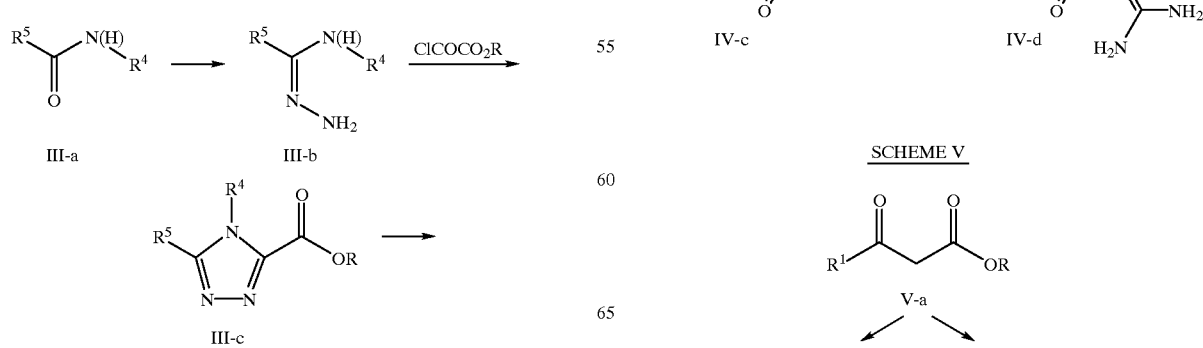

-continued

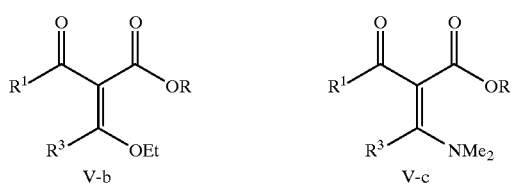

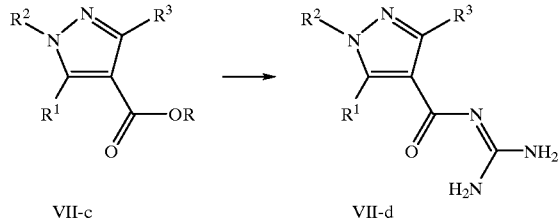

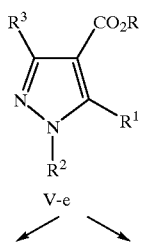

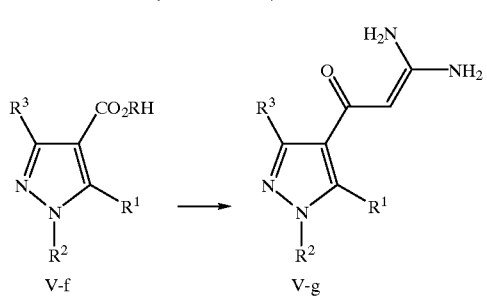

SCHEME VIII

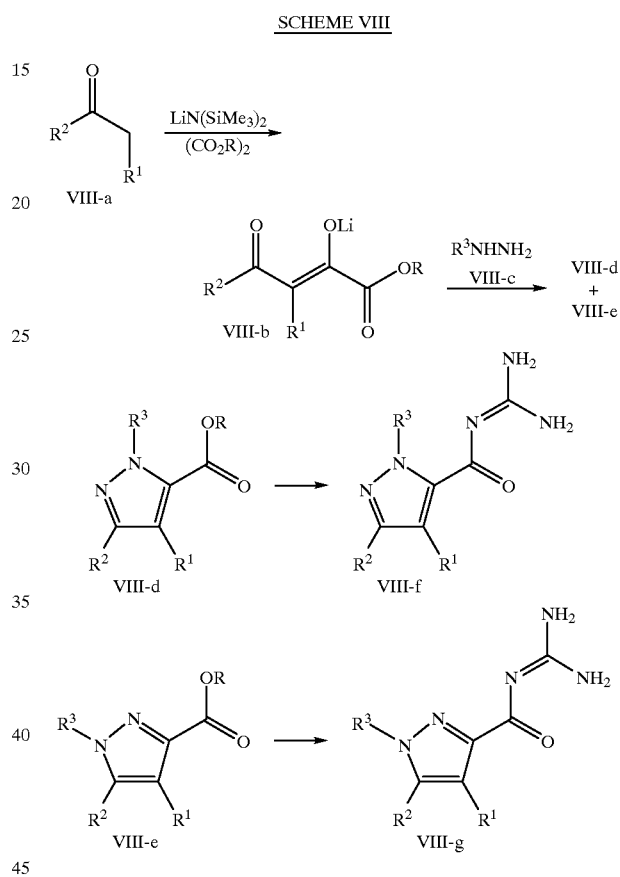

SCHEME VI

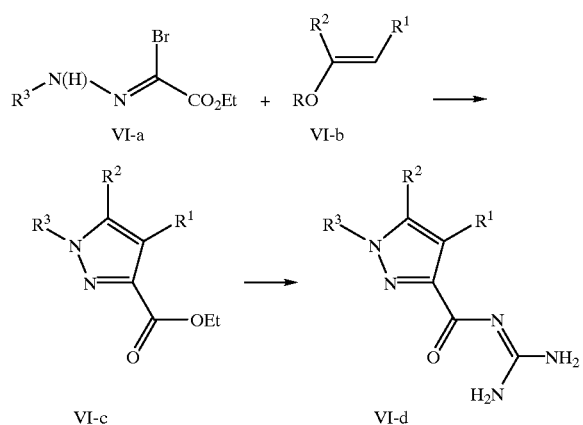

SCHEME VII

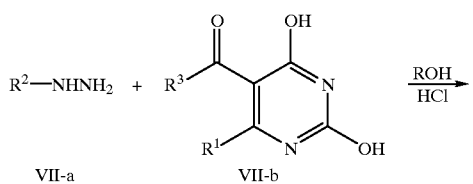

According to Scheme I, the Formula I-a compound, wherein $R^4$ is as described above for the compound of formula NHE, is dissolved or suspended in an aqueous alkali metal hydroxide solution (e.g. 1 N sodium hydroxide) along with sodium nitrite and the mixture is added to an aqueous acidic solution (e.g. 10% v/v sulfuric acid) at a pH of about 0 at a temperature of about 0° C. to about 50° C. for about 30 min to about 1 hour. The resulting mixture is filtered to yield the Formula I-b oxime. Alternatively, the Formula I-a compound is dissolved in 1:1 acetic acid/propionic acid and solid sodium nitrite is added at about 0° C. The reaction mixture is stirred at about 0° C. for about 2 hours, then poured into ice water and the Formula I-b oxime is obtained by filtration.

The Formula I-b compound is reacted with a Formula I-c compound, wherein $R^5$ is as described above for the compound of formula NHE in a protic solvent such as ethanol at a temperature of about 50° C. to about 110° C. for about 10 min to about 1 hour to form the Formula I-d hydrazone.

The Formula I-d hydrazone is cyclized and hydrolyzed to the Formula I-e triazole in an alcoholic solvent such as 2-ethoxyethanol under basic conditions (e.g., potassium hydroxide) at a temperature of about 100° C. to about 175° C. for about ½ hour to about 2 hours followed by acidification to yield the Formula I-e triazole acid.

The Formula I-e acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HBT), dicyclohexylcarbodiimide/hydroxybenzotriazole(HBT), 2-ethoxy-1-ethoxycarbonyl-1,2-dihydroquinoline (EEDQ), and diethylphosphoryicyanide. The coupling is performed in an inert solvent, preferably an aprotic solvent at a temperature of about –20° C. to about 50° C. for about 1 to about 48 hours, in the presence of excess guanidine as base. Exemplary solvents include acetonitrile, dichloromethane, dimethylformamide and chloroform or mixtures thereof.

The coupling agent may also be that agent which converts the carboxylic acid to an activated intermediate which is isolated and/or formed in a first step and allowed to react with guanidine in a second step. Examples of such coupling agents and activated intermediates are thionyl chloride or oxalyl chloride to form the add chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyidiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess guanidine in an appropriate solvent together with an appropriate base. Appropriate solvent/base combinations are for example, dichloromethane, dimethylformamide or acetonitrile or mixtures thereof in the presence of excess guanidine as base. Other appropriate solvent/base combinations include water or a ($C_1$–$C_5$)alcohol or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

According to Scheme II, the Formula II-a primary amine wherein $R^5$ is as described above for the compound of formula NHE is reacted with a Formula II-bα-diazo-βketo-ester wherein $R^4$ is as described above for the compound of formula NHE, and R is lower alkyl, in the presence of titanium tetrachloride analogously to the method described in Eguchi S. et al. *Synthesis* 1993, 793 to form the Formula II-c triazole carboxylic acid ester. The Formula II-c ester is converted directly to the acylguanidine II-d by reaction with guanidine in an alcoholic solvent at a temperature of about 60 to about 110° C., preferably refluxing methanol, for a period of 8 to 20 hours.

According to Scheme III, the Formula II-a compound wherein $R^4$ and $R^5$ are as described above for the compound of formula NHE is treated with Lawesson's reagent (i.e., 2,4-bis(4-methoxyphenyl)-1,3-dithia-2,4-diphosphetane-2,4-disulfide) in an aprotic solvent such as dimethoxyethane at a temperature of about 20° C. to about 120° C. for about one to eight hours. The resulting thioamide is treated with an alkylating agent such as methyl iodide in a polar, inert solvent such as acetone, conveniently at ambient temperature for about eight hours to about forty-eight hours. The resulting compound is reacted with anhydrous hydrazine in an alcoholic solvent at a temperature of about 0° C. to about 25° C. for about one to eight hours to provide the Formula III-b compound (analogously as described in Doyle and Kurzer, Synthesis 1974, 583).

The Formula III-b compound is treated with a monoalkyloxalyl chloride in an aprotic solvent at a temperature of about 25° C. to about 50° C. for about one to eight hours to provide the Formula III-c carboxylic ester compound wherein R is lower alkyl. The Formula III-c ester is directly coupled with guanidine in an alcoholic solvent at a temperature of about 60° C. to about 110° C., preferably refluxing methanol, for a period of eight to twenty hours, to prepare the Formula III-c triazole carbonyl guanidines.

According to Scheme IV the Formula IV-a compound wherein $R^5$ is as described above for the compound of formula NHE is treated with methyl iodide in an inert solvent, conveniently at ambient temperature for about four to twenty-four hours. The resulting compound is reacted with anhydrous $R^4$-hydrazine (wherein $R^4$ is as described above for the compound of formula NHE) in an alcoholic solvent at a temperature of about 0° C. to about 25° C. for about one to eight hours to provide the Formula IV-b amidrazone compound (analogously as described in Doyle and Kurzer, *Synthesis* 1974, 583).

The Formula IV-b compound is treated with a monoalkyloxalyl chloride in an aprotic solvent at a temperature of about 25° C. to about 50° C. for about one to eight hours to provide the Formula IV-c carboxylic ester compound wherein R is lower alkyl. The Formula IV-c ester is directly coupled with guanidine in an alcoholic solvent at a temperature of about 60° C. to about 110° C., preferably refluxing methanol, for a period of eight to twenty hours to prepare the Formula IV-d triazole carbonyl guanidines.

According to Scheme V the Formula V-a compound wherein $R^1$ is as described above for the compound of formula NHE is combined with excess $(CH_3O)_2C(R^3)N(CH_3)_2$ (N,N-dimethyl amide dimethyl acetal) wherein $R^3$ is as described above for the compound of formula NHE, optionally in the presence of an acid catalyst such as p-toluenesulfonic acid at a temperature of about 90° C. to about 110° C. for about one to about two hours to prepare the Formula V-c compound above.

The Formula V-c compound is cyclized with a Formula V-d compound, wherein $R^2$ is as described above for the compound of formula NHE, in an inert solvent such as ethanol at a temperature of about 20° C. to about 30° C. for about 5 minutes to about one hour followed by heating to a temperature of about 70° C. to about 110° C. for about two hours to about four hours to form the Formula V-f pyrazole.

Alternatively, according to Scheme V the Formula V-a compound, wherein $R^1$ is as described above for the compound of formula NHE, is combined with a triethylorthoester (i.e., $R^3C(OEt)_3$ wherein $R^3$ is as described above for the compound of formula NHE) and acetic anhydride at a temperature of about 120° C. to about 150° C. for about two to about five hours to prepare the Formula V-b compound.

The Formula V-b compound is cyclized with a Formula V-d compound, wherein $R^2$ is as described above for the compound of formula NHE, to form the Formula V-c pyrazole.

The Formula V-c pyrazole is hydrolyzed with a base such as sodium hydroxide or lithium hydroxide in a solvent such as water and/or methanol and/or THF conveniently at ambient temperature or at elevated temperature (e.g., reflux) for about one hour to about five hours to prepare the Formula V-f acid.

The Formula V-f acid is coupled with guanidine in the presence of a suitable coupling agent as described for the above coupling of the Formula I-e acid and guanidine. In one embodiment, the Formula V-f acid is activated with thionyl chloride at a temperature of about 60° C. to about 90° C. for about fifteen minutes to about two hours. The resulting activated acid chloride is combined with guanidine hydrochloride and an inorganic base (e.g., sodium hydroxide) in anhydrous tetrahydrofuran and optionally methanol and/or water. The solution is heated, conveniently at reflux, for about one hour to about eight hours to prepare the Formula V-g compound.

Alternatively according to Scheme V the Formula V-e compound can be directly converted to the Formula V-g compound by several methods. For example, the Formula V-e compound can be heated in the presence of excess guanidine, in a polar protic solvent for example, methanol or isopropanol at a suitable temperature conveniently, at reflux for about one to about seventy-two hours. This transformation may also be performed by repeatedly removing the solvent, for example removing ethanol or toluene about four times, from a mixture of the Formula V-e compound and excess guanidine at a pressure of about one to about 100 mmHg and at a temperature of about 25° C. to about 95° C. This reaction may also be performed in the absence of solvent by heating the mixture of the Formula V-e compound and excess guanidine at a temperature of about 100° C. to about 180° C., optionally at about a pressure of about 1 to about 100 mmHg for about five minutes to about eight hours.

According to Scheme VI, the Formula VI-a compound, wherein $R^3$ is as described above for the compound of formula NHE, is reacted with the Formula VI-b compound, wherein $R^1$ and $R^2$ are as described above for the compound of formula NHE, in an aprotic solvent at a temperature of about 0° C. to about 25° C. for about two hours to about twenty-four hours in the presence of an appropriate amine base, such as triethylamine, to form the Formula VI-c compound.

The resulting Formula VI-c compound is hydrolyzed and coupled with guanidine using one of the methods described in earlier Schemes, such as the method employing carbonyidiimidazole, to form the Formula VI-d compound.

According to Scheme VII, the Formula VII-a hydrazine, wherein $R^2$ is as described above for the compound of formula NHE, is reacted with the appropriate Formula VII-b compound to form the Formula VII-c pyrazole ester wherein R is lower alkyl according to the method of Bajnati, A. and Hubert-Habart, M. *Bull. Soc. Chim. France* 1988, 540. The resulting pyrazole ester is converted to the Formula VII-d acyl guanidine using the hydrolysis and coupling methods described above.

According to Scheme VIII, the Formula VIII-a compound wherein $R^2$ and $R^1$ are as described above for the compound of formula NHE is transformed to the Formula VIII-b lithium salt where R is lower alkyl according to the method described in *J. Het. Chem.* 1989, 26, 1389. The Formula VIII-b lithium salt is combined with the Formula VIII-c hydrazine, wherein $R^3$ is as described above for the compound of formula NHE, in an inert solvent such as ethanol, in the presence of a mineral acid, at a temperature of about 20° C. to about 30° C. for about five minutes to about one hour followed by heating to a temperature of about 70° C. to about 110° C. for two hours to about four hours to form both the Formula VIII-d and VIII-e pyrazoles. The Formula VIII-d and VIII-e pyrazoles are converted to the Formula VIII-f and VIII-g acyl guanidines respectively using the hydrolysis and coupling methods described above. Some of the methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

The compounds of formula I of the present invention, when used in combination with NHE-1 inhibitors, inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [(e.g. heart muscle ischemic reperfusion associated disorders, acute renal failure, or disorders induced by surgical treatment such as coronary artery bypass grafting (CABG) surgeries, vascular surgeries, organ transplantation, noncardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema.

Preferably, the compounds of formula I of this invention can be used in combination with NHE-1 inhibitors as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the compounds of formula I of this invention can be used in combination with NHE-1 inhibitors as agents for myocardial protection in patients presenting with ongoing cardiac (acute coronary syndromes, e.g. myocardial infarction or unstable angina) or cerebral ischemic events (e.g. stroke).

Preferably, the compounds of formula I of this invention can be used in combination with NHE-1 inhibitors as agents for chronic myocardial protection in patients with diagnosed coronary heart disease (e.g. previous myocardial infarction or unstable angina) or patients who are at high risk for myocardial infarction (age greater than 65 and two or more risk factors for coronary heart disease).

In addition, a combination of the compounds of formula I of this invention with NHE-1 inhibitors has a strong inhibitory effect on the proliferation of cells, for example the proliferation of fibroblast cells and the proliferation of the smooth muscle cells of the blood vessels. For this reason, the combination of the compounds of formula I of this invention with NHE-1 inhibitors of this invention is a valuable therapeutic agent for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the combination of compounds of the present invention with NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of said combination in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

Measurement of Human NHE-1 Inhibitory Activity

Methodologies for measurement of human NHE-1 activity and inhibitor potency are based on those published by Watson et al., Am. J. Physiol., 24:G229–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 minutes at 37° C. with the pH sensitive fluorescent probe BCECF (5 $\mu$M; Molecular Probes, Eugene, Oreg.). BCECF loaded cells are incubated for 30 minutes at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5) ± test combination, and NHE-mediated recovery of intracellular pH is monitored as the subsequent time-dependent increase BCECF fluorescence. The potency of the combinations of the compounds of formula I of this invention with NHE-1 inhibitors is calculated as the concentration that reduces recovery of intracellular pH by 50% ($IC_{50}$). Under these conditions reference NHE inhibitors amiloride and HOE-642 had $IC_{50}$ values for human NHE-1 of 50 $\mu$M and 0.5 $\mu$M, respectively.

As background information, it is noted that brief periods of myocardial ischemia followed by coronary artery reperfusion protects the heart from subsequent severe myocardial ischemia (Murry et al., Circulation 74:1124–1136, 1986).

The therapeutic effects of the combination of the compounds of formula I of this invention with NHE-1 inhibitors in preventing heart tissue damage resulting from an ischemic insult can be demonstrated in vitro along lines presented in Liu et al. (Cardiovasc. Res., 28:1057–1061, 1994), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described below demonstrates that a test compound or, in this case a test combination (i.e., a combination of a compound of formula I with an NHE-1 antagonist) can also pharmacologically induce cardioprotection, ie., reduced myocardial infarct size, when administered to a rabbit isolated heart. The effects of the test combination are compared to ischemic preconditioning and the A1/A3 adenosine agonist, APNEA ($N^6$-[2-(4-aminophenyl)ethyl]adenosine), that has been shown to pharmacologically induce cardioprotection in the rabbit isolated heart (Liu et al, Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2–0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, $MgSO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure $\leq$10 mmHg. Total coronary flow is also continuously monitored using an in-line flow probe and normalized for heart weight.

The heart is allowed to equilibrate for 30 minutes, over which time the heart must show stable left ventricular pressures within the parameters outlined above. If the heart rate falls below 180 bpm at any time prior to the 30 minutes period of regional ischemia, the heart is paced at about 200 bpm for the remainder of the experiment. Ischemic preconditioning is induced by total cessation of cardiac perfusion (global ischemia) for 5 minutes, followed by reperfusion for 10 minutes. The regional ischemia is provided by tightening the snare around the coronary artery branch. Following the 30 minutes regional ischemia, the snare is released and the heart reperfused for an additional 120 minutes.

Pharmacological cardioprotection is induced by infusing the test combination, i.e., a combination of a compound of formula I with an NHE-1 inhibitor, at predetermined concentrations, starting 30 minutes prior to the 30 minutes regional ischemia, and continuing until the end of the 120 minutes reperfusion period. Hearts which receive the test combination do not undergo the period of ischemic preconditioning. The reference compound, APNEA (500 nM) is perfused through hearts (which do not receive the test compound) for a 5 minutes period which ends 10 minutes before the 30 minutes regional ischemia.

At the end of the 120 minutes reperfusion period, the coronary artery snare is tightened, and a 0.5% suspension of fluorescent zinc cadmium sulfate particles (1–10 $\mu$M) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −20° C. The next day, the heart is sliced into 2 mm transverse sections from the apex to the top of the ventricles. The slices are stained with 1% triphenyl tetrazolium chloride (TTC) in phosphate-buffered saline for 20 minutes at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/AAR). All data are expressed as mean±SE and compared statistically using a Mann-Whitney non-parametric test with a Bonferroni correction for multiple comparisons. Significance is considered as p<0.05.

The results from the above in vitro test demonstrate that a combination of a compound of this invention with an NHE-1 inhibitor induce significant cardioprotection relative to the control group.

The therapeutic effects of a combination of a compound of formula I of this invention with an NHE-1 inhibitor in preventing heart tissue damage otherwise resulting from an ischemic insult can also be demonstrated in vivo along lines presented in Liu et al. (Circulation, Vol. 84:350–356, 1991) as described specifically herein. The in vivo assay tests the cardioprotection of the test combination, i.e., a compound of formula I together with an NHE-1 inhibitor, relative to the control group which receives saline vehicle. Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether the instant combination of a compound of formula I with an NHE-1 inhibitor can pharmacologically induce cardioprotection, i.e., reduced myocardial infarct size, when parenterally administered to intact, anesthetized rabbits. The effects of the combination of a compound of formula I of this invention with an NHE-11 inhibitor can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allows the affected area to reperfuse. Myocardial ischemia is evidenced by regional cyanosis; reperfusion is evidenced by reactive hyperemia.

Protocol: Once arterial pressure and heart rate have been stable for at least 30 minutes the test is started. Ischemic preconditioning is induced by occluding the coronary artery for 5 minutes followed by a 10 minutes reperfusion. Pharmacological preconditioning is induced by infusing the test combination, i.e., a combination of a compound of formula I of this invention with an NHE-1 inhibitor, over, for example, 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test combination and PIA are dissolved in saline or other suitable vehicle and delivered at 1 to 5 mg/kg, respectively.

Staining (Liu et al., Circulation 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent zinc cadmium sulphate particles (1–10 $\mu$m) Duke Scientific Corp. (Palo Alto, Calif.) is infused with the perfusate to stain all of the myocardium except the area at risk (nonfluorescent ventricle). The hearts are then quickly frozen and stored overnight at −20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a precalibrated image analyzer. To normalize the ischemic injury for differences in the area at risk between hearts, the data is expressed as the ratio of infarct area vs. area at risk (% IA/AAR). All data are expressed as Mean±SEM and compared statistically using single factor ANOVA or Mann Whitney non parametric test. Significance is considered as p<0.05.

The combination of a compound of formula I of this invention with an NHE-1 inhibitor can be tested for their utility in reducing or preventing ischemic injury in non-cardiac tissues, for example, the brain, or the liver, utilizing procedures reported in the scientific literature. The combination of a compound of formula I of this invention with an NHE-1 inhibitor in such tests can be administered by the preferred route and vehicle of administration and at the preferred time of administration either prior to the ischemic episode, during the ischemic episode, following the ischemic episode (reperfusion period) or during any of the below-mentioned experimental stages.

The benefit of the combination of NHE-1 inhibitors and compounds of formula I of this invention to reduce ischemic brain damage can be demonstrated, for example, in mammals using the method of Park, et al (Ann. Neurol. 1988;24:543–551). According to the procedure of Park, et al., adult male Sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2$>90 mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a 40% formaldehyde, glacial acetic acid and absolute methanol solution (FAM; 1:1:8, v/v/v), then the animals are decapitated and the head is stored in fixative for 24 hours. The brain is then removed, dissected, embedded in paraffin wax, and sectioned (approximately 100 sections 0.2 mm per brain). The sections are then stained with hematoxylin-eosin or with a combination of cresyl violet and Luxol fast blue, and examined by light microscopy to identify and quantitate the ischemic damage using a precalibrated image analyzer. The ischemic volumes and areas are expressed in absolute units ($mm^3$ and $mm^2$) and as a percentage of the total region examined. The effect of the compositions and methods of this invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the invention to reduce ischemic brain damage include those described by Nakayama, et al. in Neurology 1988,38:1667–1673; Memezawa, et al. in Stroke 1992,23:552–559; Folbergrova, et al. in Proc. Natl. Acad. Sci 1995,92:5057–5059; and Gotti, et al. in Brain Res. 1990,522:290–307.

The benefit of the compositions and methods of this invention to reduce ischemic liver damage can be demonstrated, for example, in mammals using the method of Yokoyama, et al. (Am. J. Physiol. 1990;258:G564–G570). According to the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MgSO_4$, 1.2 $KH_2PO_4$, 0.05 EDTA, and 11 mM glucose, plus 300 U heparin). The pH of the perfusate is maintained at 7.4 by gassing the buffer with 95% $O_2$–5% $CO_2$. Each liver is perfused at a flow rate of 20 ml/minutes in a single-pass manner for a 30 minutes washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 minutes of the 2 hour reperfusion period. The perfusate samples are assayed for the appearance of hepatocellular enzymes, for example, aspartate amino-transferase (AST), alanine amino-transferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995;22:539–545). The effect of the compositions and methods of this invention in reducing ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods and parameters which could alternatively be utilized to demonstrate the benefit of the compositions and methods of this invention in reducing ischemic liver damage include those described by Nakano, et al. (Hepatology 1995;22:539–545).

Any glycogen phosphorylase inhibitor may be used as the second compound of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays (e.g., as described hereinafter). A variety of these compounds are included in the following published PCT patent applications: PCT application publication WO 96/39384 and WO96/39385. However, other glycogen phosphorylase inhibitors will be known to those skilled in the art.

Compounds of formula I, prodrugs thereof, mutual prodrugs of the compounds of formula I with aldose reductase inhibitors, pharmaceutically acceptable salts of any of the above and pharmaceutical compositions comprising a compound of formula I, a prodrug thereof or a pharmaceutically acceptable salt of said compound or said prodrug and either (a) an aldose reductase inhibitor, a prodrug thereof or a pharmaceutically acceptable salt of said aldose reductase inhibitor or said prodrug, (b) a NHE-1 inhibitor, a prodrug thereof or a pharmaceutically acceptable salt of said NHE-1 inhibitor or said prodrug, or a glycogen phosphorylase inhibitor, a prodrug thereof or a pharmaceutically acceptable salt of said glycogen phosphorylase inhibitor or said prodrug are hereinafter referred to, collectively, as "the active compounds and comopositions of this invention."

The active compounds and compositions of this invention may be administered to a subject in need of treatment by a variety of conventional routes of administration, including orally, parenterally and topically. In general, compounds of the formula I and their pharmaceutically acceptable salts will be administered orally or parenterally at dosages between about 1 and about 50 mg/kg body weight of the subject to be treated per day, preferably from about 1 to 15 mg/kg, in single or divided doses. Mutual prodrugs of compounds of the formula I and aldose reductase inhibitors will generally be administered orally or parenterally at dosages between about 5 and about 100 mg/kg body weight of the subject to be treated per day, preferably from about 5 to about 25 mg/kg, in single or divided doses. Compositions containing both a compound of the formula I and an aldose reductase inhibitor will generally be administered orally or parenterally at dosages between about 1 and about 100 mg of each active component (i.e., the compound of formula I and the aldose reductase inhibitor) per kg body weight of the subject to be treated per day, preferably from about 1 to about 25 mg/kg. Compositions containing both a compound of formula I and a NHE-1 inhibitor will generally be administered orally or parenterally at dosages between about 1 and 100 mg of said compound of formula I per kg body weight of the subject to be treated per day and about 0.001 to 100 mg/kg/day of the NHE-1 inhibitor. An especially preferred dosage contains between about 1 and 50 mg/kg/day of said compound of formula I and between about 0.01 and 50 mg/kg/day of said NHE-1 inhibitor. Compositions containing both a compound of formula I and a glcogen phosphorylase inhibitor will generally be administered orally or parenterally at dosages between about 1 and 100 mg of said compound of formula I per kg body weight of the subject to be treated per day and 0.005 to 50 mg/kg/day of said glycogen phosphorylase inhibitor, preferably 1 and 50 mg/kg/day of said compound of formula and 0.01 to 25 mg/kg/day of said glycogen phosphorylase inhibitor and most preferably 1 and 50 mg/kg/day of said compound of formula and 0.1 to 15 mg/kg/day of said glycogen phosphorylase inhibitor. However, some variation in dosage will necessarily occur depending on the condition of the subject being treated. The person responsible for administration will, in any event, determine the appropriate dose for the individual subject.

The active compounds and compositions of this invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of formula I of this invention and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compounds and compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The active compounds and compositions of this invention may be more particularly employed in the preparation of ophthalmic solutions. Such ophthalmic solutions are of principal interest for the treatment of diabetic cataracts by topical administration. For the treatment of diabetic cataracts, the active compounds and compositions of this invention are administered to the eye in the form of an ophthalmic preparation prepared in accordance with conventional pharmaceutical practice. The ophthalmic preparation will contain a compound of the formula I, a mutual prodrug of a compound of the formula I and an aldose reductase inhibitor, or a pharmaceutically acceptable salt of such compound of formula I or prodrug, in a concentration from about 0.01 to about 1% by weight, preferably from about 0.05 to about 0.5%, in a pharmaceutically acceptable solution, suspension or ointment. In opthalmic preparations containing a combination of a compound of the formula I and an aldose reductase inhibitor, each active ingredient will be present in an amount from about 0.005 to about 1% by weight, preferably from about 0.005 to about 0.25%, in a pharmaceutically acceptable solution, suspension or ointment.

Administration of the compounds of formula I of this invention can be via any method which delivers a compound of this invention preferentially to the desired tissue (e.g., pancreatic, liver and/or cardiac tissues). These methods include oral routes, parenteral, intraduodenal routes, etc. Generally, the compounds of the present invention are administered in single (e.g., once daily) or multiple doses or via constant infusion.

The compositions of this invention comprising a compound of formula I in combination with an NHE-1 inhibitor are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The composition is therefore usefully employed prophylactically to prevent, i.e. (prospectively or prophylactically) to blunt or stem, tissue damage (e.g., myocardial tissue) in patients who are at risk for ischemia (e.g., myocardial ischemia).

Generally, a compounded of formula I of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

Thus, for example, in one mode of administration the compounds of formula I of this invention may be administered just prior to surgery (e.g., within twenty-four hours before surgery for example cardiac surgery) during or subsequent to surgery (e.g., within twenty-four hours after surgery) where there is risk of myocardial ischemia. The compounds of formula I of this invention may also be administered in a chronic daily mode.

The compounds of the present invention are generally administered in the form of a pharmaceutical composition comprising at least one of the compounds of formula I of this invention together with a pharmaceutically acceptable vehicle or diluent. Thus, the compounds of formula I of this invention can be administered individually or together in any conventional oral, parenteral, rectal or transdermal dosage form.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easton, Penn., 19th Edition (1995).

Pharmaceutical compositions according to the invention may contain for example 0.0001%–95% of the compound(s) of this invention. In any event, the composition or formulation to be administered will contain a quantity of a compound(s) according to the invention in an amount effective to treat the disease/condition of the subject being treated.

The two different compounds of this combination of this invention can be co-administered simultaneously or sequentially in any order, or as a single pharmaceutical composition comprising a compound of Formula I and an aldose reductase inhibitor as described above or a glycogen phosphorylase inhibitor as described above or a cardiovascular agent.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . ." etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of formula I of this invention generally will be administered in a convenient formulation. The following formulation examples are illustrative only and are not intended to limit the scope of the present invention.

In the formulations which follow, "active ingredient" means a compound(s) of this invention.

Formulation 1: Gelatin Capsules
Hard gelatin capsules are prepared using the following:

| Ingredient | Quantity (mg/capsule) |
| --- | --- |
| Active ingredient | 0.25–100 |
| Starch, NF | 0–650 |

-continued

Formulation 1: Gelatin Capsules
Hard gelatin capsules are prepared using the following:

| Ingredient | Quantity (mg/capsule) |
| --- | --- |
| Starch flowable powder | 0–50 |
| Silicone fluid 350 centistokes | 0–15 |

A tablet formulation is prepared using the ingredients below:

Formulation 2: Tablets

| Ingredient | Quantity (mg/tablet) |
| --- | --- |
| Active ingredient | 0.25–100 |
| Cellulose, microcrystalline | 200–650 |
| Silicon dioxide, fumed | 10–650 |
| Stearate acid | 5–15 |

The components are blended and compressed to form tablets.

Alternatively, tablets each containing 0.25–100 mg of active ingredients are made up as follows:

Formulation 3: Tablets

| Ingredient | Quantity (mg/tablet) |
| --- | --- |
| Active ingredient | 0.25–100 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.25–100 mg of active ingredient per 5 ml dose are made as follows:

Formulation 4: Suspensions

| Ingredient | Quantity (mg/5 ml) |
| --- | --- |
| Active ingredient | 0.25–100 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified Water to | 5 mL |

The active ingredient is passed through a No. 45 mesh U.S. sieve and mixed with the sodium carboxymethyl cellulose and syrup to form smooth paste. The benzoic acid solution, flavor, and color are diluted with some of the water and added, with stirring. Sufficient water is then added to produce the required volume. An aerosol solution is prepared containing the following ingredients:

Formulation 5: Aerosol

| Ingredient | Quantity (% by weight) |
| --- | --- |
| Active ingredient | 0.25 |
| Ethanol | 25.75 |
| Propellant 22 (Chlorodifluoromethane) | 74.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container. Suppositories are prepared as follows:

Formulation 6: Suppositories

| Ingredient | Quantity (mg/suppository) |
| --- | --- |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

Formulation 7: Intravenous Solution

| Ingredient | Quantity |
| --- | --- |
| Active ingredient | 25 mg–10,000 mg |
| isotonic saline | 1,000 mL |

The solution of the above ingredients is intravenously administered to a patient.

The active ingredient above may also be a combination of agents.

General Experimental Procedures

Melting points were determined on a Thomas-Hoover capillary melting point apparatus, and are uncorrected. $^1$H NMR spectra were obtained on a Bruker AM-250 (Bruker Co., Billerica, Mass.), a Bruker AM-300, a Varian XL-300 (Varian Co., Palo Alto, Calif.), or a Varian Unity 400 at about 23° C. at 250, 300, or 400 MHz for proton. Chemical shifts are reported in parts per million ( ) relative to residual chloroform (7.26 ppm), dimethylsulfoxide (2.49 ppm), or methanol (3.30 ppm) as an internal reference. The peak shapes are denoted as follows: s, singlet; d, doublet; t, triplet; q, quartet; m, multiplet; c, complex; br, broad. Low-resolution mass spectra were obtained under thermospray (TS$^+$) conditions on a Fisons (now Micromass) Trio 1000 Mass Spectrometer (Micromass Inc., Beverly, Mass.), under chemical-ionization (CI) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer. Optical rotations were obtained on a Perkin-Elmer 241 MC Polarimeter (Perkin-Elmer, Norwalk, Conn. using a standard path length of 1 dcm at about 23° C. at the indicated concentration in the indicated solvent.

Liquid column chromatography was performed using forced flow (flash chromatography) of the indicated solvent on either Baker Silica Gel (40 μm, J. T. Baker, Phillipsburg, N.J.) or Silica Gel 60 (EM Sciences, Gibbstown, N.J.) in glass columns or using low nitrogen or air pressure in Flash 40™ or Flash 12™ (Biotage, Charlottesville, Va.) cartridges. Radial chromatography was performed using a Chromatron (Harrison Research, Palo Alto, Calif.). The terms "concentrated" and "evaporated" refer to removal of solvent using a rotary evaporator at water aspirator pressure or at similar pressures generated by a Büchi B-171 Vacobox (Brinkmann Instruments, Inc., Westbury, N.Y.) or a Büchi B-177 Vacobox with a bath temperature equal to or less than 50° C. Reactions requiring the use of hydrogen gas at pressures greater than 1 atmosphere were run using a Parr hydrogen apparatus (Parr Instrument Co., Moline, Ill.). Unless otherwise specified, reagents were obtained from commercial sources. The abbreviations "d", "h", and "min" stand for "day(s)", "hour(s)", and "minute(s)", respectively.

EXAMPLE 1

4-[2-(1R-Hydroxy-ethyl)-pyrimidin-4-yl]-piperazine-1-sulfonic acid dimethylamide

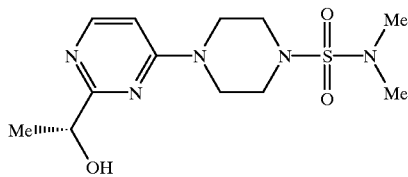

Step A. (R)-2-Methoxy-propionitrile

A mixture of 2-methoxy-propionamide (prepared according to Freudenberg and Market, Chem. Ber., 1927, 60, 2453; 3.0 g, 29.1 mmol), phosphorous pentoxide (4.13 g, 29.1 mmol), and dry sand (3.0 g) was heated to 160° C. in a distillation apparatus and the distillate was collected (1.01 g, 44%); $[\alpha]_D$+139.2 (c=1, methanol); $^1$H NMR (CDCl$_3$, 300 MHz) δ1.5 (d, 3H), 3.45 (s, 3H), 4.14 (q, 1H).

Step B. (R)-2-Methoxy-propionimidic acid ethyl ester hydrochloride

Hydrogen chloride gas was passed into an icecold solution of (R)-2-methoxy-propionitrile (prepared according to the method of Example 1, Step A, 9.91 g, 116.5 mmol) in anhydrous ethanol (100 mL) until the solution was saturated with the gas. The reaction was stored in a refrigerator over night. The excess ethanol was removed under vacuum to obtain the title compound of Example 1, Step B as a deliquescent solid (19.5 g, 100% yield); $[\alpha]_D$+46.4 (c=1, methanol); $^1$H NMR (CDCl$_3$, 300 MHz) δ1.4 (d, 3H), 3.4 (s, 1H), 3.7 (q, 2H), 4.8 (q, 1H), 6.2 (b, 1H).

Step C. (R)-2-Methoxy-propionamidine

A solution of (R)-2-methoxy-propionimidic acid ethyl ester hydrochloride in ethanol was cooled in an ice-bath and gaseous ammonia was passed into the solution until the reaction was saturated with ammonia. The reaction mixture was stirred over night. Excess ethanol was removed to obtain a syrupy liquid, which was triturated with diethyl ether (100 mL). The resulting solid was filtered to collect the title compound of Example 1, Step C (12.2 g), m.p.60–75° C.; $[\alpha]_D$+45.4 (c=1, methanol); $^1$H NMR (CDCl$_3$, 300 MHz) δ1.4 (d, 3), 3.4 (s, 3H), 3.7 (q, 1H), 5.8 (b, 1H), 6.5 (b, 1H).

Step D. (R)-2-Methoxymethyl4-hydroxy-pyrimidine

A mixture of (R)-2-Methoxy-propionamidine (prepared according to the method of Example 1, Step C, 10.0 g, 72.15 mmol), 2-ethoxycarbonyl ethenolate (prepared according to Preparation One, Step C, 19.93 g, 144.3 mmol), and water (50 mL) was stirred at room temperature for 24 h. The reaction was neutralized by addition of sufficient conc. HCl to adjust the pH to around 7.0 and extracted with methylene chloride. The extract was dried over anhydrous sodium sulfate, evaporated to dryness and the residue was chromatographed over silica gel. Elution with a mixture of 95:5 methylene chloride and methanol and evaporation of the eluent afforded a thick viscous oil (1.7 g); $[\alpha]_D$+76.4 (c=1, methanol); $^1$H NMR (CDCl$_3$, 300 MHz) δ1.51 (d, 3H), 3.44 (s, 3H), 4.29 (q, 1H), 7.91 (d, 1H), 11.00 (b, 1H).

Step E. (R)-2-(1-Methoxyethyl)-pyrimidin-4-yl-methanesulfonate

To an ice-cold solution of (R)-2-methoxymethyl-4-hydroxy-pyrimidine (1.69 g, 10.95 mmol) in methylene chloride (10 mL) was first added triethylamine (1.7 mL, 12.05 mmol) and then mesyl chloride (1.38 g, 12.05 mmol). The reaction was stirred at ice temperature for 20 min and then was warmed to room temperature. After 1 h, the reaction was quenched with saturated aqueous sodium bicarbonate solution, the organic layer was collected and it was washed with water (10 mL), dried over sodium sulfate, filtered and the filtrate was evaporated to afford an oil (2.11 g, 83%). $[\alpha]_D$+69.2 (c=1, methanol); $^1$H NMR (CDCl$_3$, 300 MHz) δ1.52 (d, 3H), 3.38 (s, 3H), 3.62 (s,3H), 4.53 (q, 1H), 7.00 (d, 1H), 8.80 (d, 1H).

Step F. (R)-4-[2-(1-Methoxy-ethyl)-pyrimidin-4-yl]-piperazine-1-sulfonic acid dimethylamide To a solution of (R)-2-(1-methoxyethyl)-pyrimidin-4-yl-methanesulfonate (prepared according to the method of Example 1, Step E, 2.11 g, 9.1 mmol) in tetrahydrofuran (20 mL) was added dimethylsulfamoyl piperazine (prepared according to the method disclosed in U.S. Pat. No. 2,748, 129, 1.94 g, 10 mmol) followed by triethylamine (1.4 mL, 10 mmol). The reaction was refluxed for 15 h, and evaporated to an oily residue. This was extracted with ethyl acetate (20 mL) and the extract was washed first with a saturated aqueous solution of sodium bicarbonate and then with water (10 mL). The ethyl acetate extract was dried over sodium sulfate, filtered, and the filtrate was evaporated to a crude product, which was chromatographed over silica gel. Elution with a mixture of 9:1 ethyl acetate and methanol and evaporation of the solvents gave the title compound of Example 1, Step F (1.75 g, 59%); mp, 65–70° C., $[\alpha]_D$+ 54.4° (c=1, methanol); $^1$H NMR (CDCl$_3$, 300 MHz) δ1.48 (d, 3H), 2.89(s,6H, 3.31(m, 4H), 3.37 (s, 3H), 3.78(m, 4H), 4.34(q, 1H), 6.41(d, 1H), 8.30(d, 1H).

Step G. 4-[2-(1R-Hydroxy-ethyl)-pyrimidin-4-yl]-piperazine-1-sulfonic acid dimethylamide To an ice-cold solution of 4-[2-(1-Methoxy-ethyl)-pyrimidin-4-yl]-piperazine-1-sulfonic acid dimethylamide (prepared according to the method of Example 1, Step F, 1.75 g, 5.31 mmol) in methylene chloride (53 mL) was added boron tribromide (10.6 mL, 10.6 mmol) and the reaction was stirred for 1 h. The reaction mixture was allowed to warm up to room temperature, was quenched with a saturated aqueous solution of sodium bicarbonate. The methylene chloride layer was washed with water (20 mL), dried over sodium sulfate, filtered and the filtrate was evaporated to a solid residue, which was crystallized from a mixture of isopropyl ether and methylene chloride to obtain the title compound of Example 1 as a white solid (642 mg, 38%); mp, 103–105° C.; [α]$_D$+16.1° (c=1, methanol); $^1$H NMR (CDCl$_3$, 300 MHz) d 1.48 (d, 6H), 2.83 (s, 3H), 3.31 (m, 4H), 3.74 (m, 4H), 4.70 (q, 1H), 6.40 (d, 1H), 8.21 (d, 1H); MS (Cl) M$^{+1}$316.

EXAMPLE 2

Example 2
4-[2-(1R-Hydroxy-ethyl)-pyrimidin-4-yl]-piperazine-1-sulfonic acid dimethylamide

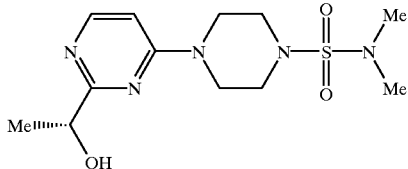

Step A
4-[2-Formyl-pyrimidin-4-yl]-piperazine-1-sulfonic acid dimethylamide.

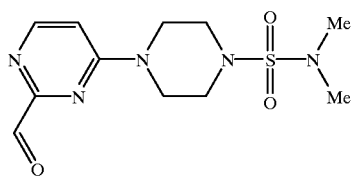

To a solution of 4-[2-hydroxy-methyl)-pyrimidin-4-yl]-piperazine-1-sulfonic acid dimethylamide (prepared according to the method disclosed in U.S. Pat. No. 5,138,058, 12.12 g, 40.2 mmol) in methylene chloride (100 mL) was added a solution of oxalyl chloride (3.9 mL, 44.2 mmol) and the reaction mixture was cooled to −78° C. To reaction mixture was added a solution of DMSO (6.27 mL, 88.4 mmol) in methylene chloride (20 mL) dropwise, to keep the reaction temperature at or below −70° C. After 2 h, triethylamine (28.0 mL, 88.4 mmol) was added dropwise and the reaction was allowed to come to room temperature. The reaction mixture was diluted with water (200 mL), and the collected organic layer was washed with saturated sodium bicarbonate solution. The washed organic layer was collected, dried over sodium sulfate, filtered and the filtrate was evaporated to a solid. The solid was triturated with ether (20 mL) and the mixture was filtered to afford the title compound of Example 2, Step A (10.84 g, 94%); mp 124–127° C.

Step B. 4-[2-(1RS-Hydroxy-ethyl-pyrimidin-4-yl]-piperazine-1-sulfonic acid dimethylamide To a −5° C. cooled solution of 4-(2-formyl-pyrimidin-4-yl)-piperazine-1-sulfonic acid dimethylamide (prepared according to the method of Example 2, Step A, 419 g, 14 mmol) in dry tetrahydrofuran (100 mL) was added an ether solution methyl magnesium bromide (7.6 mL, 23.1 mmol). After 20 min, the reaction was allowed to warm up to room temperature and then refluxed for 30 min. After cooling the reaction to room temperature, it quenched with saturated ammonium chloride solution and then extracted with ethyl acetate (2×50 mL). The organic layer was collected, dried over sodium sulfate, filtered and the filtrate was evaporated to afford a pale yellow solid (4.21 g, 95%); mp 115–116° C.

Step C.
R-1-[4-(4-Dimethylsulfamoyl-piperazin-1-yl)-pyrimidin-2-yl]-ethyl acetate.

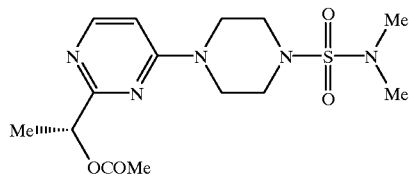

To a solution containing 4-[2-(1-(RS)-hydroxy-ethyl)-pyrimidin-4-yl]-piperazine-1-sulfonic acid dimethylamide (prepared according to the method of Example 2, Step B. 0.9 g, 2.86 mmol), dimethoxyethane (5.7 mL) and vinyl acetate (10.5 mL) was added Lipase P30 (90 mg, 10%) and the reaction mixture was stirred at room temperature for 14 days. It was filtered, the filtrate was evaporated to brown oil, which was chromatographed over silica gel. Elution with a 95:5 mixture of ethyl acetate and methanol and evaporation of the eluent gave the title compound of Example 2, Step C as a clear oil (220 mg, 43%); [α]$_D$+41.9 (c=1, methanol $^1$H NMR (CDCl$_3$, 300 MHz) δ1.55(d, 6H), 2.2(s, 3H), 2.9(s, 6H), 3.3 (m, 4H), 3.8(m, 4H), 6.35(q, 1H), 6.4(d, 1H), 8.25(d, 1H).

Step D. 4-[2-(1R-Hydroxy-ethyl)-pyrimidin-4-yl]-piperazine-1-sulfonic acid dimethylamide A solution containing R-1-[4-(4-Dimethylsulfamoyl-piperazin-1-yl)-pyrimidin-2-yl]-ethyl acetate (prepared according to the method of Example 2, Step C, 200 mg, 0.56 mmol), dioxane (4 mL), methanol (0.5 mL), and potassium hydroxide (4 drops, 20% aq. solution) was stirred at room temperature for 1 h. It was diluted with water (10 mL), extracted with ethyl acetate (2×10 mL), the organic layer collected, dried over sodium sulfate and the filtrate was evaporated to obtain the title compound of Example 2 as a white solid having the same identifying characteristics as set forth for the compound of Example 1.

EXAMPLE 3

4-[2-(1R-Hydroxy-ethyl)-pyrimidin-4-yl]-piperazine-1-sulfonic acid dimethylamide Step A. 1 (R)-(4-Piperazin-1-yl-pyrimridin-2-yl)-ethyl butyrate (R,S) 2-Hydroxyethyl 4-hydroxy pyrimidine (prepared according to Preparation One, Step D, 21.75 g, 155.2 mmol) was added to dioxane (650 mL) containing vinyl butyrate (17.72 g, 310 mmol) and the mixture heated to 50° C. To the resulting solution was added lipase P30 4.35 g) and the heating was continued for 24 h. The reaction mixture was filtered and the filtrate was evaporated to obtain a thick syrupy liquid residue. The residue was partitioned between methylene chloride (300 mL) and water (600 mL) and the methylene chloride layer was collected, dried over anhydrous sodium sulfate and then filtered. The filtrate was evaporated to obtain the title compound of Example 3, Step A as a colorless liquid (9.35 g, 86%); [α]$_D$+29.5 (c=1, methanol); $^1$H NMR (CDCl$_3$, 300 MHz) δ0.95 (t, 3H), 1.65 (m, 5H), 2.4 (m, 2H), 5.65 (q, 1H), 6.45 (d, 1H), 8.0 (d, 1H).

Step B. (R)-1-(4-Piperazin-1-yl-pyrimridin-2-yl)-ethyl butyrate

To a ice cold solution of (R)-1-(4-hydroxy-pyrimidin-2-yl)-ethyl butyrate (10.5 g, 50.0 mmol) and triethylamine (6.06 g, 97.8 mmol) in dichloromethane (100 mL) was added methanesulfonyll chloride (6.29 g, 55.0 mmoles) dropwise and stirred for 1.5 h at ambient temperature. The mixture was washed successively with saturated bicarbonate and water, dried over magnesium sulfate and filtered. The filtrate was evaporated to give (R)-1-(4-methanesulfonyloxy-pyrimidin-2-yl)-ethyl acetate 12.6 g (91%) as an oil. This was dissolved in tetahydrofuran (100 mL), and to the solution was added piperazine (7.57 g, 88.0 mmol) and stirred at ambient temperature for 12.0 hr. The mixture was filtered and the filtrate concentrated then pumped under reduced pressure for 3 h to give the title compound as a oil 10.2 g (73%). $^1$H NMR (CDCl$_3$, 300 MHz) δ0.95 (t, 3H), 1.56 (d, 3H), 1.68 (m, 2H), 2.48 (t, 2H), 2.83 (m, 4H), 3.63 (m, 4H), 5.53 (q, 1H), 6.35 (d, 1H), 8.21 (d, 1H); MS (TS) 279 (MH$^+$).

Step C
R-1-[4-(4-Dimethylsulfamoyl-piperazin-1-yl)-pyrimidin-2-yl]- ethyl butyrate.

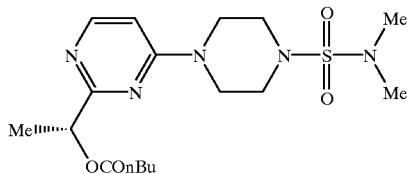

To a solution of 1(R)-[4-piperazin-1-yl)-pyrimidin-2-yl]-ethyl butyrate (prepared according to the method of Example 3, Step B, 1.49 g, 5.0 mmol), triethylamine (0.61 g, 6.0 mmol), and tetrahydrofuran (20.0 mL) was added N,N-dimethylsulfamoyl chloride (0.86 g, 6.0 mmol) at ambient temperature and stirred for 2 h. The mixture was diluted with water and extracted twice with ethyl acetate. The ethyl acetate extract was washed once with water (10 mL), dried over magnesium sulfate, filtered, and the filtrate was concentrated to obtain the title compound of Example 3, Step B as an oil (0.72 g, 87%); $^1$H NMR (CDCl$_3$, 300 MHz) d 0.95 (t, 3H), 1.55(d, 6H), 1.55 (d, 3H), 1.6–1.7 (m, 4H) 2.42 (t, 2H), 3.2 (m, 1H), 3.45 (m, 4H), 3.74 (m, 4H), 5.4 (q, 1H), 6.4 (d, 1H), 8.1 (d, 1H);.

Step C. 4-[2-(1R-Hydroxy-ethyl)-pyrimidin-4-yl]-pipirazine-1-sulfonic acid dimethylamide R-1-[4-(4-dimethylsulfamoyl-piperazin-1-yl)-pyrimidin-2-yl]-ethyl butyrate (prepared according to the method of Example 3, Step B, 230 mg, 0.60 mmol) was combined with conc. hydrochloric acid (5.0 mL) and stirred at ambient temperature for 6 h, diluted with water, pH of the solution was adjusted to 9.0 with 6N aqueous sodium hydroxide and extracted twice with ethyl acetate. The extract was washed once with water, dried over magnesium sulfate, filtered, and the filtrate was concentrated to an oil which was purified by flash chromatography (9:1 methylene chloride: methanol). Evaporation of the eluent gave an oil which was crystallized from isopropyl ether to obtain the title compound of Example 3 having the same identifying characteristics as set forth for the compound of Example 1.

EXAMPLE 4

(R)-{1-4-[4-(Propane-2-sulfonyl)-piperazin-1-yl]-pyrimidin-2-yl]-ethanol

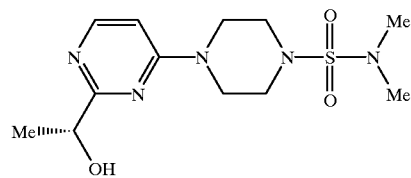

Step A
(R)-{1-4-[4-(Propane-2-sulfonyl)-piperazin-1-yl]-pyrimidin-2-yl}-ethyl butyrate.

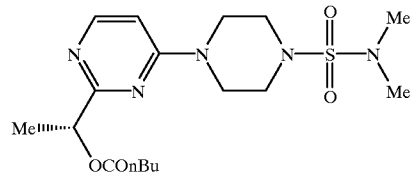

To a solution of 1R-(4-piperazin-1-yl-pyrimidin-2-yl)-ethyl butyrate (prepared according to the method of Example 3, Step B, 2.1 g, 7.5 mmol), triethylamine (0.91 g, 9.0 mmol), in methylene chloride (37 mL) was added isopropylsulfonyl chloride (1.3 g, 9.0 mmol) at ambient temperature and stirred for 14 h. The mixture was washed with water (2×20 mL), dried over magnesium sulfate, filtered, and the filtrate was concentrated to give R-1-{4-[4-(propane-2-sulfonyl)-piperazin-1-yl]-pyrimidin-2-yl}-ethyl butyrate as a clear oil 2.05 g (87%); $^1$H NMR (CDCl$_3$, 300 MHz) δ0.95 (t, 3H), 1.42 (d, 6H), 1.55 (d, 3H), 1.6–1.7 (m, 4H) 2.42 (t, 2H), 3.2 (m, 1H), 3.45 (m, 4H), 3.74 (m, 4H), 5.4 (q, 1H), 6.4 (d, 1H), 8.1 (d, 1H); MS (Cl) M$^{+1}$ 385.

Step B
(R)-{1-4-[4-(Propane-2-sulfonyl)-piperazin-1-yl]-pyrimidin-2-yl]-ethanol.

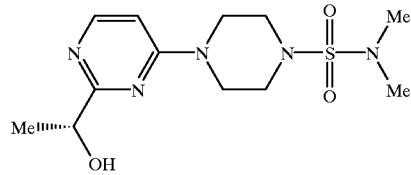

To a solution of (R)-1-{4-[4-(propane-2-sulfonyl)-piperazin-1-yl]-pyrimidin-2-yl}-ethyl butyrate (prepared according to the method of Example 4, Step A, 1.9 g, 4.92 mmol) in methanol (30 mL) was added at ambient temperature 6.0 N aqueous potassium hydroxide (5.0 mL). After stirring for 3.0 h the solution was diluted with methylene chloride (50 mL) and washed twice with water (10 mL). The organic layer was separated dried over magnesium sulfate, filtered, and the filtrate concentrated to a viscous oil which was purified by flash chromatography using a 9:1 mixture of methylene chloride and methanol. Evaporation of the solvents gave a solid which was crystallized from cyclohexane to give the title compound of Example 4 as a white solid (1.2 g, 77%); mp: 65° C.–66° C.; $^1$H NMR (CDCl$_3$, 300 MHz) δ1.4 (d, 6H), 1.54 (d, 3H ), 3.23 (m, 1H), 3.4 (m, 4H), 3.6–3.8 (m, 4H), 4.75 (m, 1H), 6.46 (d, 1H), 8.12 (d, 1H); MS (Cl) M$^{+1}$ 315; [α]$_d$+14.5 (c 1.0, MeOH).

EXAMPLE 5

4-[2-(1S-hydroxy-ethyl)-pyrimidin-4-yl]-piperazine-1-sulfonic acid dimethylamide

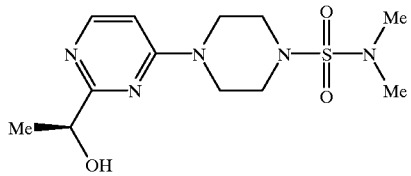

Step A. 1(S)-(4-hydroxy-pyrimidin-2-yl)-ethyl butyrate

To a solution of 2-(S-1-hydroxyethyl)-3H-pyrimidin-4-one (prepared according to the method of Preparation Four, 1.40 g 10 mmol), triethylamine (2.22 g, 22 mmol) in methylene chloride (20 mL) was added N,N-dimethylaminopyridine (0.06 g 0.5 mmol) followed by butyric anhydride (1.74 g, 11 mmol) at 0° C. After stirring at ambient temperature for 1.0 h the mixture was washed with water, and the methylene chloride layer was dried over magnesium sulfate and filtered. The filtrate was concentrated to give the title compound as an oil (1.97 g, 94%); $^1$H NMR (CDCl$_3$, 300 MHz) δ0.94 (t, 3H), 1.49 (d, 3H) 1.68 (m, 2H), 2.38 (t, 2H), 5.64 (q, 1H), 6.38 (d, 1H), 8.21 (d, 1H); MS (Cl) 2.11 (MH$^+$); [α]$_d$–44.3 (c 1.0, MeOH).

Step B. 1(S)-(4-Piperazin-1-yl-pyrimidin-2-yl-ethyl butyrate

To an ice cold solution of 1-(S)-(4-hydroxy-pyrimidin-2-yl)ethyl butyrate (prepared according to the method of Example 5, Step A, 0.42 g, 2.0 mmol) and triethylamine (0.20 g, 2.2 mmol) in methylene chloride (10 mL) was added mesyl chloride (0.25 g, 2.1 mmol) dropwise and stirred for 1.5 h. The mixture was washed successively with saturated bicarbonate and water, and the organic layer was dried over anhydrous magnesium sulfate. It was filtered and evaporated to give1-(S)-(4-methanesulfonyloxy-pyrimidin-2-yl)ethyl butyrate as an oil. The oil was dissolved in tetahydrofuran (10 mL), and to the solution was added piperazine (0.69 g, 8.0 mmol) and stirred at ambient temperature for 4 hr. The mixture was filtered and the filtrate was concentrated to obtain a crude product which was purified by flash chromatography (9:1 methylene chloride:methanol) to give the title compound of Example 5, Step B as an oil (0.50 g, 90%);$^1$H NMR (CDCl$_3$, 300 MHz) δ0.95 (t, 3H), 1.51 (d, 3H) 1.68 (m, 2H), 2.66 (t, 2H), 2.83 (m, 4H), 3.63 (m, 4H), 5.54 (q, 1H), 6.38 (d, 1H), 8.24 (d, 1H); MS (Cl) 251 (MH$^+$).

Step C
4-[2-(1S-hydroxy-ethyl)-pyrimidin-4-yl]-piperazine-1-sulfonic acid dimethylamide.

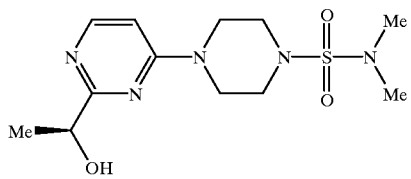

To a solution of 1(S)-[4-piperazin-1-yl)-pyrimidin-2-yl]-ethyl butyrate (prepared according to the method of Example 5, Step B, 0.52 g, 1.8 mmol), triethylamine (0.21 g, 2.0 mmol), and tetrahydrofuran (5.0 mL) was added N,N-dimethylsulfamoyl chloride (0.29 g, 1.8 mmol) at ambient temperature and stirred for 2 h. The mixture was diluted with water and extracted twice with ethyl acetate. The extract was washed once with water (10 mL), dried over magnesium sulfate, filtered, and the filtrate concentrated to an oil. The oil was dissolved in conc. hydrochloric acid (3.0 mL) stirred at ambient temperature for 6 h, diluted with water and pH of the solution was adjusted to 9.0 with 6N aqueous sodium hydroxide. The reaction mixture was extracted with ethyl acetate (2×10 mL) and the extract was washed once with water (10 mL), dried over magnesium sulfate, filtered, and the filtrate was concentrated to afford an oil which was purified by flash chromatography (95:5 methylene chloride/methanol) to give an oil. Trituration of the oil with isopropyl ether afforded the title compound of Example 5 as a white solid (0.16 g, 28.2%); mp, 99° C.–100° C.; $^1$H NMR (CDCl$_3$, 300 MHz) δ1.48 (d, 6H), 2.83 (s, 3H), 3.32 (m, 4H), 3.74 (m, 4H), 4.69 (q, 1H), 6.41 (d, 1H), 8.21 (d, 1H); MS (Cl) M$^{+1}$ 316; [a]$_d$–16.9 (c 1.0, MeOH).

EXAMPLE SIX

[4-Oxo-3-(5-trifluoromethyl-benzothiazol-2-ylmethyl)-3,4-dihydro-phthalzin-1-yl]-acetic acid (R)-1-[4-(4-dimethylsulfamoyl-piperazin-1-yl)-pyrimidin-2-yl]-ethyl ester.

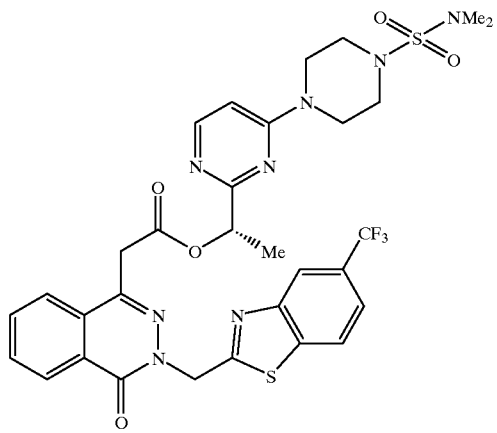

To a slurry of [4-oxo-3-(5-trifluoromethyl-benzothiazol-2-ylmethyl)-3,4dihydro-phthalazin-1-yl]-acetic acid (zopolrestat, 0.21 g, 0.50 mmol) in dichloromethane (10 mL) was added N,N-dimethylaminopyridine (0.06 g, 0.50 mmol) and stirred until homogenous. 1-(3-dimethylaminopropyl)-3-ethylcarbodiimide hydrochloride (0.54 g, 2.82 mmol) was added followed by [2-(1R-hydroxy-ethyl)-pyrimidin-4-yl]-piperazine-1-sulfonic acid dimethylamide (prepared by the method of Example 1, 0.16 g, 0.5 mmol) and stirred at ambient temperature for 16 hours. The mixture was washed once with water, once with saturated aqueous sodium chloride, dried over magnesium sulfate and filtered. The filtrate was concentrated to an ooil which was purified by flash chromatography (98:2 dichloromethane:methane) to give the title compound as a white foam, 0.31 (86%). $^1$H NMR ((CDCl$_3$, 300 MHz) δ1.52 (d, 3H), 2.82 (s, 6H), 3.38–3.86 (m, 8H), 4.27 (m, 2H), 5.21 (q, 1H), 6.35 (d, 1H), 6.68 (d, 1H), 7.68 (m, 1H), 7.71–7.90 (m, 4H), 8.18 (d, 1H), 8.46 (m, 1H); mp: 105–109° C.; MS (Cl) 746 (MH$^+$); [a]$_D$+49.2 (c 1.0, MeOH).

Preparation One 2-(1RS-Hydroxy-ethyl)-3H-pyrimidin-4-one

Step A. 2-hydroxytropionimidic acid ethyl ester hydrochloride

A solution of (RS)-lactonitrile (378 9, 5.32 mol) in ethyl ether (1.46 L) and ethanol (0.34 L) was saturated with hydrogen chloride gas at 0° C.–5° C. for 0.5 h and kept at 5° C. for 60 h. The solid was filtered off and washed twice with ethyl ether to give 2-hydroxypropionimidic acid ethyl ester hydrochloride as a solid (815 g, 99%); mp, 165–168° C.; $^1$H NMR (DMSO-d6, 300 MHz) δ1.38 (t, 3H), 4.49(q, 1H), 6.55–7.11 (bs, 1H).

Step B. 2-hydroxy-propionamidine hydrochloride

A suspension of 2-hydroxypropionimidic acid ethyl ester hydrochloride (prepared according to the method of Preparation One, Step A, 751 g, 4.87 mol) in ethanol (3.75 L) at 0° C. was saturated with ammonia gas maintaining the internal temperature below 5° C. for 1 h. It was then stirred at ambient temperature for 18 h. The solid was filtered off and dried under vacuum at 40° C. to obtain a solid. The filtrate was concentrated to one half its volume and a second crop of solid was collected which was dried under vacuum and combined with the fist crop to afford 2-hydroxy-propionamidine hydrochloride as a yellow solid (608 g, 99%); mp, 134–138° C.; $^1$H NMR (DMSO-d6, 300 MHz) δ1.33 (t, 3H), 4.42(q, 1H), 6.25–6.88 (bs, 1H), 8.72–9.25 (bs, 3H).

Step C. 2-ethoxycarbonyl ethenolate

To a suspension of sodium hydride (60% dispersion in oil) (269 g, 16.7 mol) in isopropyl ether (12 L) was slowly added ethyl acetate (1280 g, 14.2 mol) at such a rate as to maintain an internal temperature of 45° C. Ethyl formate (2232 g, 30.13 mol) then added dropwise at 42° C. and stirred at ambient temperature for 18 h. The mixture was filtered and washed with ethyl ether (2×300 mL), with hexanes (500 mL) and the solid was dried to give sodium 2-ethoxycarbonyl ethenolate as a white solid (1930 g, 99%); $^1$H NMR (DMSO-d6, 300 MHz) δ1.03 (t.3H), 3.86 (q, 2H), 4.08(d, 1H), 8.03 (d, 1H).

Step D. 2-(1RS-Hydroxy-ethyl)-3H-pyrimidin-4-one

To a solution of sodium 2-ethoxycarbonyl ethenolate (prepared according to the method of Preparation One, Step C, 1301 g, 9.42 mol) in water (1.3 L) was added an aqueous solution of 2-hydroxy-propionamidine hydrochloride (prepared according to the method of Preparation One, Step B, 610 g, 4.9 mol) in water (1.3 L) at ambient temperature and stirred for 48 h. The solution was adjusted to pH 7.0 with acetic acid and then continuously extracted with chloroform for 48 h. The extract was dried over sodium sulfate and filtered. The filtrate was concentrated to a solid which was slurried in ethyl ether, filtered and the solid residue dried to give the title compound of Preparation One (232 g, 38%); mp: 121–124° C.; $^1$H NMR (DMSO-d6, 300 MHz) ??1.45 (d, 1H), 4.42(q, 1H), 6.25–6.88 (bs, 1H).

Preparation Two 1-(R)-4-hydroxy-pyrimridin-2-yl-ethyl acetate (R,S) 2-Hydroxyethyl 4-hydroxy pyrimidine (prepared according to Preparation One, Step D, 2.1 g, 15.07 moles) was added to dioxane (63 mL) containing vinyl acetate (4.3 g, 50 moles) and the mixture heated to 50° C. To the resulting solution was added lipase P30 (0.21 g) and the heating was continued for 24 h. The reaction mixture was filtered and the filtrate was evaporated to obtain a thick syrupy liquid residue. The residue was chromatographed over silica gel and flash eluted with a mixture of 95:5 methylene chloride and methanol. Evaporation of the collected eluent gave the title compound as a colorless liquid (0.97 g, 92%); [α]$_D$+39.9° (c=1, methanol); $^1$H NMR (CDCl$_3$, 300 MHz) δ1.61 (d, 3H), 2.2 (s, 3H), 5.65 (q, 1H), 6.35 (d, J=6 Hz, 1H), 7.97 (d, 1H), 11.94 (s, 1H).

Preparation Three 1-(S)-(4-Piperazin-1-yl-pyrimidin-2-yl)-ethyl butyrate

To an ice cold solution of 1-(S)-(4-hydroxy-pyrimidin-2-yl)-ethyl butyrate (0.42 g, 2.0 mmol) and triethylamine (0.20 g, 2.2 mmol) in methylene chloride (10 mL) was added mesyl chloride (0.25 g, 2.1 mmol) dropwise and stirred for 1.5 h. The mixture was washed successively with saturated bicarbonate and water, and the organic layer dried over anhydrous magnesium sulfate. It was, filtered and evaporated to give 1-(S)-(4-methanesulfonyloxy-pyrimidin-2-yl)-ethyl as an oil. The oil was dissolved in tetahydrofuran (10 mL), and to the solution was added piperazine (0.69 g, 8.0 mmol) and stirred at ambient temperature for 4 hr. The mixture was filtered and the filtrate was concentrated to obtain a crude product which was purified by flash chromatography (9:1 methylene chloride/methanol) to give the title compound as a oil 0.50 g (90%). $^1$H NMR (CDCl$_3$, 300 MHz) δ0.95 (t, 3H), 1.51 (d, 3H) 1.68 (m, 2), 2.66 (t, 2H), 2.83 (m, 4H), 3.63 (m, 4H), 5.54 (q, 1H), 6.38 (d, 1H), 8.24 (d, 1H); MS (Cl) 251 (MH$^+$).

Preparation Four 2-(1R-hydroxy-ethyl)-3H-pyrimidin-4-one and 2-(1S-Hydroxy-ethyl)-3H-pyrimidin-4-one 2-(1RS-hydroxyethyl)-3H-pyrimidin-4-one (30 g) was separated into its individual enatiomers by preparative HPLC. Multiple injections of 0.4 g was loaded onto a chiralpak AS column (5 cm×50 cm) and eluted with hexane/ethanol (85:15) at flow rate of 75 mL/min. Fractions were analyzed using a AS 25 cm analytical column eluting with heptane:ethanol:diethyl amine (85:15:0.05). The fastest eluting fractions (7.2 min) were pooled and evaporated to give 2-(1S-hydroxy-ethyl)-3H-pyrimidin-4-one as an oil (9.9 g, 66% recovery); $^1$H NMR (CDCl$_3$, 300 MHz) ? 1.51 (d, 3H), 5.54 (q, 1H), 6.38 (d, 1H), 8.24 (d, 1H); MS (Cl) 251 (MH$^+$); [α]$_d$–69.8 (c 1.0, MeOH).

The slower eluting fractions (9.1 min) were pooled and evaporated to give 2-(1R-hydroxy-ethyl)-3H-pyrimidin-4-one as an oil (12.4 g, 80% recovery); $^1$H NMR (CDCl$_3$, 300 MHz) δ1.51 (d, 3H), 5.54 (q, 1H), 6.38 (d, 1H), 8.24 (d, 1H); MS (Cl) 251 (MH$^+$); [α]$_d$+65.8 (c 1.0, MeOH).

96-Well Microtiter Plate Kinetic Assay for Sorbitol Dehydrogenase

Principle

Reaction 1:

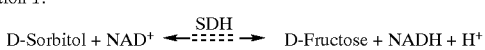

D-Sorbitol + NAD$^+$ $\xrightleftharpoons{\text{SDH}}$ D-Fructose + NADH + H$^+$ Reaction 2:

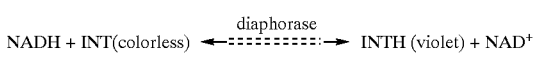

NADH + INT(colorless) $\xrightleftharpoons{\text{diaphorase}}$ INTH (violet) + NAD$^+$ Reagents
Reagent 1

100 mM potassium phosphate buffer, Ph 7.0

6.8 g KH2PO4 (Fischer no. P285-500) and 8.7 g K2HPO4 (Fischer no. P288-500) are dissolved in ~990 ml distilled water, the pH is adjusted to 7.0 with 5 N KOH, and distilled water added to bring volume to 1000 ml.

Reagent 2

β-Nicotinamide Adenine Dinucleotide (NAD$^+$) Sigma no. N-7129

Reagent 3

Diaphorase (EC 1.8.1.4 from Clostridium kluyveri) Sigma no. D-5540

Reagent 4

Iodonitrotetrazolium violet (INT) dye Sigma no. 1-8377

A 10 mM solution is prepared by dissolving 253 mg INT in a final volume of 50 ml distilled water. Heating for 30 minutes at about 50° C. while stirring is required for complete dissolution.

Reagent 5

Recombinant human or rat SDH solutions

Pan Ver no. R1820 or R1828, respectively. about 0.5 mg/ml

Test Solution

Compounds are dissolved in 20% (v/v) DMSO at a concentration of 5 mM. Serial dilutions are performed with 20% DMSO to yield 10× desired final concentrations.

Working Reagent 22.4 mg NAD$^+$, 14.8 mg Diaphorase and 21 μl human rSDH or 146 μl rat rSDH is added to 25 ml phosphate buffer. After mixing on a vortex mixer, 2.7 ml INT solution is added.

Procedure

25 μl of DMSO or test solutions are added to each well of a 96well microtiter plate. 200 μl working reagent is added to each well and allowed to incubate at room temperature for 15 minutes. 25 μl of 20 mM D-sorbitol is added to start the reaction. Absorbance at 495 nm is monitored for 10 minutes at room temperature. The rate of increase in $A_{495}$ for each well containing compound is compared to that for wells containing only DMSO. Percent Inhibition is calculated as:

$$\% \text{ Inhibition} = \frac{\text{Uninihibted } A_{495} - \text{Inhibited } A_{495}}{\text{Unhibited } A_{495}} \times 100$$

Final Concentrations

| Potassium Phosphate | 90 mM, pH 7.0 |
|---|---|
| NAD$^+$ | 1 mM |
| INT | 1 mM |
| Sorbitol | 2 mM |

SDH 2 nM (human rSDH) or 14 nM (rat rSDH)

IC$_{50}$, nM (human SDH)

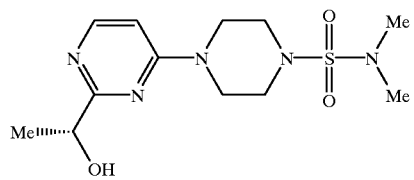

27 ± 4

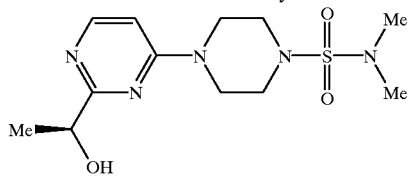

486 ± 24

4-[2-(1R-hydroxy-ethyl)-pyrimidin-4-yl]-piperazine-1-sulfonic acid dimethylamide 4-[2-(1S-hydroxy-ethyl)-pyrimidin-4-yl]-piperazine-1-sulfonic acid dimethylamide

What is claimed is:

1. A compound of formula I,

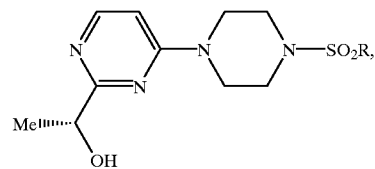

I a prodrug thereof or a pharmaceutically acceptable salt of said compound or said prodrug, wherein:

R is N,N-dimethylamino or isopropyl.

2. The compound of claim 1 of the formula

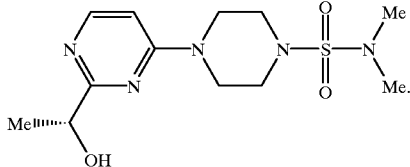

3. The compound of claim 1 of the formula

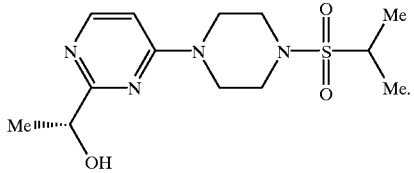

4. A pharmaceutical composition comprising a compound of claim 1, a prodrug thereof or a pharmaceutically acceptable salt of said compound or said prodrug and a pharmaceutically acceptable carrier or diluent.

5. A method of inhibiting sorbitol dehydrogenase in a mammal in need of such inhibition comprising administering to said mammal a sorbitol dehydrogenase inhibiting amount of a compound of claim 1, a prodrug thereof or a pharmaceutically acceptable salt of said prodrug or said compound.

6. A method of treating diabetes in a mammal suffering from diabetes comprising administering to said mammal an effective amount of a compound of claim 1, a prodrug thereof or a pharmaceutically acceptable salt of said prodrug or said compound.

7. A method of treating or preventing diabetic complications in a mammal comprising administering to said mammal an effective amount of a compound of claim 1, a prodrug thereof or a pharmaceutically acceptable salt of said prodrug or said compound.

8. A method of claim 7 wherein said mammal is suffering from diabetes.

9. A method of claim 8 wherein said diabetic complication is diabetic neuropathy.

10. A method of claim 8 wherein said diabetic complication is diabetic nephropathy.

11. A method of claim 8 wherein said diabetic complication is diabetic retinopathy.

12. A method of claim 8 wherein said diabetic complication is foot ulcers.

13. A method of claim 8 wherein said diabetic complication is a cardiovascular condition.

14. A pharmaceutical composition comprising a compound of claim 1, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

15. A composition of claim 14 additionally comprising a pharmaceutically acceptable carrier or diluent.

16. A method of treating diabetes in a mammal suffering from diabetes comprising administering to said mammal an effective amount of a compound of claim 1, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

17. A method of treating or preventing diabetic complications in a mammal comprising administering to said mammal an effective amount of a compound of claim 1, a prodrug thereof or a pharmaceutically acceptable salt of said prodrug or said compound, and an aldose reductase inhibitor (ARI), a prodrug of said ARI or a pharmaceutically acceptable salt of said ARI or said prodrug.

18. A method of claim 17 wherein said mammal is suffering from diabetes.

19. A method of claim 17 wherein said diabetic complication is diabetic neuropathy.

20. A method of claim 17 wherein said diabetic complication is diabetic nephropathy.

21. A method of claim 17 wherein said diabetic complication is diabetic retinopathy.

22. A method of claim 17 wherein said diabetic complication is foot ulcers.

23. A method of claim 17 wherein said diabetic complication is a cardiovascular condition.

24. A pharmaceutical composition comprising a compound of claim 1, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

25. A method of treating ischemia in a mammal suffering from ischemia comprising administering to said mammal an effective amount of a compound of claim 1, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

26. A method of claim 25 wherein said ischemia is perioperative myocardial ischemia.

27. A method of treating or preventing diabetic complications in a mammal comprising administering to said mammal an effective amount of a compound of claim 1, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

28. A method of claim 27 wherein said mammal is suffering from diabetes.

29. A method of claim 27 wherein said diabetic complication is diabetic neuropathy.

30. A method of claim 27 wherein said diabetic complication is diabetic nephropathy.

31. A method of claim 27 wherein said diabetic complication is diabetic retinopathy.

32. A method of claim 27 wherein said diabetic complication is foot ulcers.

33. A method of claim 27 wherein said diabetic complication is a cardiovascular condition.

34. A method of treating diabetes in a mammal suffering from diabetes comprising administering to said mammal an effective amount of a compound of claim 1, a prodrug thereof or a pharmaceutically acceptable salt of said prodrug or said compound, and a sodium hydrogen ion exchange (NHE-1) inhibitor, a prodrug of said NHE-1 inhibitor or a pharmaceutically acceptable salt of said NHE-1 inhibitor or said prodrug.

35. A kit comprising:
   a. a compound of claim 1, a prodrug thereof or a pharmaceutically acceptable salt of said prodrug or said compound in a first unit dosage form;
   b. an aldose reductase inhibitor, a prodrug thereof or a pharmaceutically acceptable salt of said prodrug or said aldose reductase inhibitor in a second unit dosage form; and
   c. a container.

36. A kit comprising:
   a. a compound of claim 1, a prodrug thereof or a pharmaceutically acceptable salt of said prodrug or said compound in a first unit dosage form;
   b. a sodium hydrogen ion exchange (NHE-1) inhibitor, a prodrug thereof or a pharmaceutically acceptable salt of said prodrug or said NHE-1 inhibitor in a second unit dosage form; and
   c. a container.

37. A method of inhibiting sorbitol dehydrogenase in a mammal in need thereof comprising administering to said mammal a pharmaceutical composition of claim 4.

38. A method of treating ischemia in a mammal suffering from ischemia comprising administering to said mammal a pharmaceutical composition of claim 24.

39. A method of treating or preventing diabetic complications in a mammal comprising administering to said mammal a pharmaceutical composition of claim 4.

40. A method of treating or preventing diabetic complications in a mammal comprising administering to said mammal a pharmaceutical composition of claim 14.

41. A method of treating or preventing diabetic complications in a mammal comprising administering to said mammal a pharmaceutical composition of claim 24.

42. A compound of the formula II,

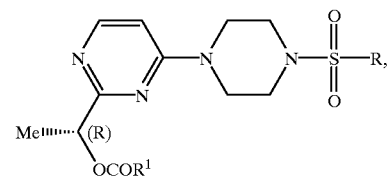

wherein:

R is N,N-dimethylamino or isopropyl; and $R^1$ is $(C_1-C_4)$alkyl, benzyl or phenyl, said benzyl and phenyl being optionally substituted with up to three $(C_1-C_4)$alkyl, $(C_1-C_4)$alkoxy, halo or nitro.

43. A compound of the formula III,

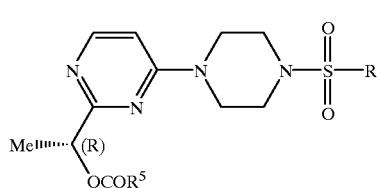

III wherein:

R is N,N-dimethylamino or isopropyl; and $R^5$ is

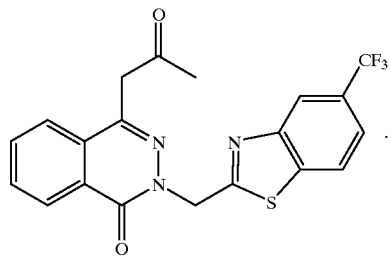

44. A compound of the formula IV:

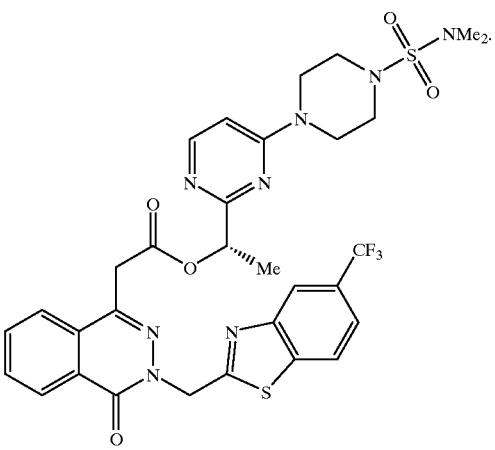

45. A pharmaceutical composition comprising a compound of claim 1, a prodrug thereof or a pharmaceutically acceptable salt of said prodrug or said compound, and a glycogen phosphorylase inhibitor (GPI), a prodrug of said GPI or a pharmaceutically acceptable salt of said GPI or said prodrug.

46. A kit comprising:
  a. a compound of claim 1, a prodrug thereof or a pharmaceutically acceptable salt of said prodrug or said compound in a first unit dosage form;
  b. a glycogen phosphorylase inhibitor (GPI), a prodrug thereof or a pharmaceutically acceptable salt of said prodrug or said GPI in a second unit dosage form; and
  c. a container.

* * * * *